United States Patent
Bothma et al.

(10) Patent No.: US 11,173,263 B2
(45) Date of Patent: Nov. 16, 2021

(54) RESPIRATORY SUPPORT SYSTEM AND BLOWER FOR RESPIRATORY SUPPORT SYSTEM

(71) Applicant: Fisher & Paykel Healthcare Limited, Auckland (NZ)

(72) Inventors: Johannes Nicolaas Bothma, Auckland (NZ); Alex Young, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 300 days.

(21) Appl. No.: 16/097,575

(22) PCT Filed: Apr. 27, 2017

(86) PCT No.: PCT/IB2017/052427
§ 371 (c)(1),
(2) Date: Oct. 29, 2018

(87) PCT Pub. No.: WO2017/191534
PCT Pub. Date: Nov. 9, 2017

(65) Prior Publication Data
US 2019/0160240 A1 May 30, 2019

Related U.S. Application Data

(60) Provisional application No. 62/350,093, filed on Jun. 14, 2016, provisional application No. 62/331,750, filed on May 4, 2016.

(51) Int. Cl.
*A61M 16/00* (2006.01)
*F04D 29/42* (2006.01)
(Continued)

(52) U.S. Cl.
CPC ...... *A61M 16/0069* (2014.02); *A61M 16/022* (2017.08); *A61M 16/024* (2017.08);
(Continued)

(58) Field of Classification Search
CPC .... F04D 29/4246; F04D 29/40; F04D 29/406; F04D 29/4226; F04D 29/4233;
(Continued)

(56) References Cited

U.S. PATENT DOCUMENTS 5,584,339 A * 12/1996 Hong .................... H01L 23/467
165/122
9,381,318 B2 7/2016 Kenyon et al.
(Continued)

FOREIGN PATENT DOCUMENTS

CN 1826151 8/2006
CN 101502690 8/2009
(Continued)

OTHER PUBLICATIONS

International Search Report and Written Opinion for PCT/IB2017/052427 dated Jul. 17, 2017 in 13 pages.

*Primary Examiner* — Jan Christopher L Merene
*Assistant Examiner* — Brian T Khong
(74) *Attorney, Agent, or Firm* — Knobbe, Martens, Olson & Bear, LLP

(57) ABSTRACT

A respiratory system including a dual outlet blower. One of a first and a second outlet of the blower provides a flow of gases to one of a pair of nasal outlets of a nasal interface and the other one of the first and second outlets provides a flow of gases to the other one of the pair of nasal outlets of the nasal interface. In an alternative embodiment, one of the first and second outlets provides a flow of gases to a nasal outlet of an oro-nasal interface and the other one of the first and second outlets provides a flow of gases to an oral outlet of the oro-nasal interface.

16 Claims, 24 Drawing Sheets

(51) Int. Cl.
*A61M 16/06* (2006.01)
*F04D 17/16* (2006.01)
*F04D 27/00* (2006.01)
*A61M 16/16* (2006.01)
*A61M 16/10* (2006.01)

(52) U.S. Cl.
CPC ...... *A61M 16/0666* (2013.01); *A61M 16/109* (2014.02); *A61M 16/16* (2013.01); *F04D 17/16* (2013.01); *F04D 27/001* (2013.01); *F04D 29/4246* (2013.01); *A61M 2016/0027* (2013.01); *A61M 2016/0036* (2013.01); *A61M 2016/0039* (2013.01); *A61M 2205/15* (2013.01); *A61M 2205/3365* (2013.01); *A61M 2230/46* (2013.01)

(58) Field of Classification Search
CPC .. F04D 29/424; F04D 29/4253; F04D 29/426; F04D 29/50; F04D 29/506; F04D 29/52; F04D 17/08; F04D 17/10; F04D 17/12; F04D 17/122; F04D 17/125; F04D 17/127; F04D 17/14; F04D 17/16; F04D 17/164; F04D 17/165; F04D 27/001; F04D 27/002; F04D 27/005; F04D 27/0246; F04D 27/0269; A61M 16/0069; A61M 16/0066; A61M 16/0063; A61M 16/006; A61M 16/0057; A61M 16/109; A61M 16/1095; A61M 16/106; A61M 16/0666; A61M 16/0672; A61M 16/024; A61M 16/026; A61M 16/022; A61M 16/16; A61M 2016/003; A61M 2016/0027; A61M 2016/0033; A61M 2016/0039; F05D 2250/52; F05D 2250/53; F05D 2270/3013

See application file for complete search history.

(56) References Cited

U.S. PATENT DOCUMENTS

| | | | | |
|---|---|---|---|---|
| 9,841,034 B2* | 12/2017 | Jia | ........................ | F04D 29/4226 |
| 2002/0119044 A1* | 8/2002 | O'Connor, Jr. | ...... | F04D 29/4246 |
| | | | | 415/204 |
| 2003/0228213 A1* | 12/2003 | Bikos | .................. | F04D 25/166 |
| | | | | 415/101 |
| 2004/0115039 A1* | 6/2004 | Botros | ................. | F04D 25/166 |
| | | | | 415/101 |
| 2005/0011523 A1* | 1/2005 | Aylsworth | ........ | A61M 16/0069 |
| | | | | 128/207.18 |
| 2006/0024160 A1* | 2/2006 | Horng | ................ | F04D 29/4226 |
| | | | | 415/206 |
| 2006/0174885 A1* | 8/2006 | Aylsworth | ........ | A61M 16/0069 |
| | | | | 128/206.11 |
| 2006/0198741 A1* | 9/2006 | Wu | ........................ | F04D 29/424 |
| | | | | 417/406 |
| 2008/0152479 A1* | 6/2008 | Horng | ................... | F04D 29/661 |
| | | | | 415/119 |
| 2010/0044468 A1* | 2/2010 | Granger | ................ | F04D 25/163 |
| | | | | 239/304 |
| 2010/0142146 A1* | 6/2010 | Hwang | ............... | F04D 29/4226 |
| | | | | 361/695 |
| 2010/0209271 A1* | 8/2010 | Yoo | ........................ | A47L 5/22 |
| | | | | 417/423.2 |
| 2011/0027078 A1* | 2/2011 | Pan | ........................ | F04D 29/083 |
| | | | | 415/206 |
| 2011/0073110 A1* | 3/2011 | Kenyon | ............... | F04D 25/0606 |
| | | | | 128/204.18 |
| 2011/0108033 A1 | 5/2011 | Schaetzl | | |
| 2012/0157794 A1* | 6/2012 | Goodwin | .......... | A61M 16/0683 |
| | | | | 600/301 |
| 2012/0234323 A1 | 9/2012 | Connor | | |
| 2012/0285454 A1 | 11/2012 | Nibu et al. | | |
| 2013/0064660 A1* | 3/2013 | Hong | ..................... | F04D 29/282 |
| | | | | 415/206 |
| 2013/0101451 A1* | 4/2013 | Dickinson | .............. | F04D 17/162 |
| | | | | 417/423.7 |
| 2014/0099195 A1* | 4/2014 | Jun | ...................... | F04D 25/0613 |
| | | | | 415/182.1 |
| 2014/0154067 A1* | 6/2014 | Shih | ....................... | F04D 29/646 |
| | | | | 415/201 |
| 2015/0217073 A1 | 8/2015 | Nitta et al. | | |
| 2015/0260198 A1* | 9/2015 | Aiello | .................... | F04D 29/281 |
| | | | | 415/206 |
| 2015/0300368 A1* | 10/2015 | Hsu | ....................... | F04D 29/703 |
| | | | | 415/108 |
| 2016/0076555 A1* | 3/2016 | Krejci | ................... | F04D 29/284 |
| | | | | 415/177 |
| 2016/0369811 A1* | 12/2016 | Ling | ..................... | F04D 29/661 |
| 2016/0369819 A1* | 12/2016 | Lofy | ................... | F04D 29/4246 |
| 2017/0002830 A1* | 1/2017 | Ma | ........................ | F04D 29/663 |
| 2017/0175747 A1* | 6/2017 | Gundel | .................... | F04D 17/16 |
| 2018/0298914 A1* | 10/2018 | Nakamura | .......... | F04D 29/4246 |

FOREIGN PATENT DOCUMENTS

| | | |
|---|---|---|
| CN | 202031849 | 11/2011 |
| CN | 102596299 | 7/2012 |
| CN | 202468462 | 10/2012 |
| CN | 103687638 | 3/2014 |
| EP | 1305083 | 5/2008 |
| EP | 2 085 106 | 8/2009 |
| EP | 2299122 | 3/2011 |
| JP | S62-113898 | 5/1987 |
| WO | WO 200202169 | 1/2002 |
| WO | WO 2008/077003 | 6/2008 |

* cited by examiner

RESPIRATORY SUPPORT SYSTEM AND BLOWER FOR RESPIRATORY SUPPORT SYSTEM

CROSS REFERENCE TO RELATED APPLICATIONS

The present application is a national phase of PCT Application No. PCT/IB2017/052427, filed Apr. 27, 2017, which claims the priority benefit of U.S. Provisional Application Nos. 62/331,750, filed May 4, 2016, and 62/350,093, filed Jun. 14, 2016, which are hereby incorporated in their by reference in its entirety.

TECHNICAL FIELD

The present disclosure relates to a respiratory support system comprising a blower for providing a flow of respiratory gases to a patient or user, and a blower for a respiratory support system.

BACKGROUND ART

A blower (gases supply unit) is used to generate a flow of respiratory gases to be provided to a patient or user for the treatment of respiratory health issues. For example, continuous positive airway pressure devices and/or systems for treating sleep apnea comprise a blower for providing a flow of positive pressure air to support a user's airways. In many cases, a blower is used together with a humidifier to provide a flow of humidified gases to a user. A respiratory system may include an integrated gases supply device which comprises both a humidifier and a blower. A prior art integrated gases supply device is described in international patent publication WO2013/009193.

A schematic representation of a modular respiratory system is provided in FIG. 1. The system comprises a blower 2 in fluid communication with a humidifier 4 via a conduit. A further conduit 3 provides a flow of gases generated by blower 2 and humidified by the humidifier to a user 1 via a patient interface 5. A further schematic representation is provided in FIG. 2, representing an integrated blower and humidification unit 6 that comprises a blower 2 and humidifier 4 in a single integrated unit.

In the systems of FIGS. 1 and 2, the patient interface 5 may be a full face mask that provides a flow of gases to the user's airways via the user's mouth and nose, or may be an oral interface or a nasal interface. A nasal interface may seal against the users face around the nose, or may engage with the user's nares, in either a sealing or non-sealing way. For example a nasal cannula may provide a pair of prongs to engage with the user's nares without forming an air tight seal. Alternatively a nasal interface may comprise a pair of nasal pillows that sealingly engage the nares of a user.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE DISCLOSURE

It is an object of the present invention to provide an improved blower or respiratory support system, or to at least provide the industry or public with a useful choice.

In accordance with at least one of the embodiments disclosed herein, a blower for providing a flow or respiratory gases comprises a respiratory (support) system comprising a dual outlet blower, wherein one of a first and a second outlet of the blower provides a flow of gases to one of a pair of nasal outlets of a nasal interface and the other one of the first and second outlets provides a flow of gases to the other one of the pair of nasal outlets of the nasal interface, or wherein one of the first and second outlets provides a flow of gases to a nasal outlet of a oro-nasal interface and the other one of the first and second outlets provides a flow of gases to an oral outlet of the oro-nasal interface.

In some embodiments, the blower comprises:
an impeller, and
a housing comprising an impeller chamber in which the impeller rotates and the first outlet and the second outlet, the first outlet arranged to direct a flow of gases from the housing when the impeller rotates in a first direction of rotation, and the second outlet arranged to direct a flow of gases from the housing when the impeller rotates in an opposite second direction of rotation.

In some embodiments, with rotation of the impeller in the first direction of rotation, a flow of gases from the first outlet is greater than a flow of gases from the second outlet, and
with rotation of the impeller in the second direction of rotation, a flow of gases from the second outlet is greater than a flow of gases from the first outlet.

In some embodiments, rotation of the impeller in a first direction of rotation generates a first flow of gases from the first outlet and a second flow of gases from the second outlet, and
rotation of the impeller in an opposite second direction of rotation generates the first flow of gases or a third flow of gases from the second outlet and the second flow of gases or a fourth flow of gases from the first outlet, and
the flow rate of the first flow of gases is greater than the flow rate of the second flow of gases, and the flow rate of the third flow of gases is greater than the flow rate of the fourth flow of gases.

In some embodiments, the flowrate of the first flow of gases is substantially the same as the flowrate of the third flow of gases.

In some embodiments, the blower comprises a motor for driving rotation of the impeller, and the housing comprises the impeller chamber and a motor chamber for supporting the motor within the housing.

In some embodiments, the blower comprises a first impeller and a second impeller, and the housing comprises a first impeller chamber in which the first impeller rotates and a second impeller chamber in which the second impeller rotates, and
wherein the first and second impellers are rotationally coupled to rotate together, the first impeller for generating a flow of gases from the first outlet when the first and second impellers rotate in the first direction of rotation, and the second impeller for generating a flow of gases from the second outlet when the first and second impellers rotate in the second direction of rotation.

In some embodiments, the blower comprises a motor for driving rotation of the first and second impellers, the motor comprising a rotor and a stator, wherein the first and second impellers are rotationally coupled to the rotor.

In some embodiments, the rotor is positioned axially between the first and second impellers, and wherein the housing comprises a motor chamber for the motor located axially between the first and second impeller chambers.

In some embodiments, the impeller is a centrifugal impeller.

In some embodiments, the housing comprises a volute chamber receiving a flow of gases from the impeller chamber.

In some embodiments, the first outlet extends substantially tangentially from the housing with respect to a first direction of rotation of the impeller, and the second outlet extends substantially tangentially from the housing with respect to an opposite second direction of rotation of the impeller.

In some embodiments, the volute chamber receives a flow of gases from the first and second impeller chambers.

In some embodiments, the housing comprises:
a first volute chamber to receive a flow of gases from the first impeller chamber, the first outlet arranged to direct the first flow of gases from the first volute chamber, and
a second volute chamber to receive a flow of gases from the second impeller chamber, the second outlet arranged to direct the second flow of gases from the second volute chamber.

In some embodiments, the first and second outlets are axial outlets

In some embodiments, the first outlet is an axial outlet at a first side of the blower and the second outlet is an axial outlet at a second side of the blower.

In some embodiments, the housing comprises a first stator ring and a second stator ring, each stator ring comprising a plurality of volute paths, the first axial outlet comprising the volute paths of the first stator ring, and the second axial outlet comprising the volute paths of the second stator ring.

In some embodiments, each stator ring comprises a plurality of curved vanes, each said volute path separated from an adjacent volute path in the stator ring by a said curved vane.

In some embodiments, each stator ring comprises the plurality of curved vanes spaced circumferentially apart radially outside of or adjacent to or at the radial outer perimeter of the impeller or a respective one of a first impeller and a second impeller.

In some embodiments, the blower comprises:
an impeller, and
a housing comprising an impeller chamber in which the impeller rotates and the first outlet and the second outlet, wherein:
rotation of the impeller in a first direction of rotation generates a first flow of gases from the first outlet and a second flow of gases from the second outlet, and
rotation of the impeller in an opposite second direction of rotation generates the first flow of gases or a third flow of gases from the second outlet and the second flow of gases or a fourth flow of gases from the first outlet, and
the flow rate of the first flow of gases is greater than the flow rate of the second flow of gases, and the flow rate of the third flow of gases is greater than the flow rate of the fourth flow of gases.

In some embodiments, the blower comprises:
an impeller, and
an impeller housing comprising the first outlet and the second outlet, the first outlet extending substantially tangentially from the housing with respect to a first direction of rotation of the impeller, and the second outlet extending substantially tangentially from the housing with respect to an opposite second direction of rotation of the impeller.

In some embodiments, the system comprises the nasal interface, the interface comprising a first nasal outlet for providing a flow of respiratory gases to a user via one of the user's nares, and a second nasal outlet for providing a flow of respiratory gases to the user via the other one of the user's nares, wherein the first outlet of the blower is in fluid communication with the first nasal outlet of the nasal interface, and the second outlet of the blower is in fluid communication with the second nasal outlet of the nasal interface,
wherein rotation of an impeller of the blower in a first direction of rotation generates a flow of gases to the first nasal outlet of the nasal interface, and rotation of the impeller in a second direction of rotation generates a flow of gases to the second nasal outlet of the nasal interface.

In some embodiments, the system comprises a sensing arrangement to determine occlusion of one of the nares of the user and a controller to control the direction of rotation of the impeller in response,
wherein if the sensing arrangement detects one of the user's nares is at least partially occluded, the sensing arrangement causes the impeller to rotate in one of the first and second directions of rotation to generate a flow to the other one of the user's nares, and vice versa.

In some embodiments, the sensing arrangement comprises a pressure or flow sensor to detect a pressure or flow to or at the user's nares to determine if one or other of the user's nares is at least partially occluded.

In some embodiments, the sensing arrangement comprises:
a first pressure or flow sensor to detect a pressure or flow to or at one of the user's nares to determine if the one of the user's nares is at least partially occluded, and
a second pressure or flow sensor to detect a pressure or flow to or at the other one of the user's nares to determine if the other one of the user's nares is at least partially occluded.

In some embodiments, the system comprises the oro-nasal interface comprising the nasal outlet for providing a flow of respiratory gases to a user via at least one of the user's nares, and the oral outlet for providing a flow of respiratory gases to the user via the user's mouth, and
wherein the first outlet of the blower housing is in fluid communication with the nasal outlet of the oro-nasal interface, and the second outlet of the blower housing is in fluid communication with the oral outlet of the oro-nasal interface,
wherein rotation of an impeller of the blower in a first direction of rotation generates a flow of gases to the nasal outlet, and rotation of the impeller in a second direction of rotation generates a flow of gases to the oral outlet.

In some embodiments, the system comprises a controller configured to control the direction of rotation of the impeller based on at least one of a user input, a measured condition, or a predetermined condition.

In accordance with at least one of the embodiments disclosed herein, a dual axial outlet blower comprises:
an impeller, and
a housing comprising an impeller chamber in which the impeller rotates, an axial inlet, and a first axial outlet and a second axial outlet, wherein, with rotation of the impeller in the first direction of rotation, a flow of gases from the first outlet is greater than a flow of gases from the second outlet, and with rotation of the impeller in the second direction of rotation, a flow of gases from the second outlet is greater than a flow of gases from the first outlet.

In some embodiments, rotation of the impeller in a first direction of rotation generates a first flow of gases from the first outlet and a second flow of gases from the second outlet, and rotation of the impeller in an opposite second direction of rotation generates the first flow of gases from the second outlet and the second flow of gases from the first outlet, and the flow rate of the first flow of gases is greater than the flow rate of the second flow of gases.

In some embodiments, the blower comprises a motor for driving rotation of the impeller, and the housing comprises the impeller chamber and a motor chamber for supporting the motor within the housing.

In some embodiments, the impeller is a centrifugal impeller.

In some embodiments, the first outlet is an axial outlet at a first side of the blower and the second outlet is an axial outlet at a second side of the blower.

In some embodiments, the blower comprises a first impeller and a second impeller, and the housing comprises a first impeller chamber in which the first impeller rotates and a second impeller chamber in which the second impeller rotates, and wherein the first and second impellers are rotationally coupled to rotate together, the first impeller generating a flow of gases from the first outlet when the first and second impellers rotate in the first direction of rotation, and the second impeller generating a flow of gases from the second outlet when the first and second impellers rotate in the second direction of rotation.

In some embodiments, the blower comprises a motor for driving rotation of the first and second impellers, the motor comprising a rotor and a stator, wherein the first and second impellers are rotationally coupled to the rotor.

In some embodiments, the rotor is positioned axially between the first and second impellers, and wherein the housing comprises a motor chamber for the motor located axially between the first and second impeller chambers.

In some embodiments, the housing comprises a first stator ring and a second stator ring, each stator ring comprising a plurality of volute paths, the first axial outlet comprising the volute paths of the first stator ring, and the second axial outlet comprising the volute paths of the second stator ring.

In some embodiments, the blower is without a volute chamber other than the volute paths of the stator rings.

In some embodiments, each stator ring comprises a plurality of curved vanes, each said volute path separated from an adjacent volute path in the stator ring by a said curved vane.

In some embodiments, each stator ring comprises the plurality of curved vanes spaced circumferentially apart radially outside of or adjacent to or at the radial outer perimeter of the impeller or a respective one of a first impeller and a second impeller.

In accordance with at least one of the embodiments disclosed herein, a dual axial outlet blower comprises:
an impeller, and
a housing comprising:
an impeller chamber in which the impeller rotates, and
a first axial outlet and a second axial outlet, the first outlet arranged to direct a flow of gases from the housing when the impeller rotates in a first direction of rotation, and the second outlet arranged to direct a flow of gases from the housing when the impeller rotates in an opposite second direction of rotation.

In some embodiments, the impeller is a centrifugal impeller.

In some embodiments, the first outlet is an axial outlet at a first side of the blower and the second outlet is an axial outlet at a second side of the blower.

In some embodiments, the blower comprises a first impeller and a second impeller, and the housing comprises a first impeller chamber in which the first impeller rotates and a second impeller chamber in which the second impeller rotates, and wherein the first and second impellers are rotationally coupled to rotate together, the first impeller generating a flow of gases from the first outlet when the first and second impellers rotate in the first direction of rotation, and the second impeller generating a flow of gases from the second outlet when the first and second impellers rotate in the second direction of rotation.

In some embodiments, the housing comprises a first stator ring and a second stator ring, each stator ring comprising a plurality of volute paths, the first axial outlet comprising the volute paths of the first stator ring, and the second axial outlet comprising the volute paths of the second stator ring.

In some embodiments, the blower is without a volute chamber other than the volute paths of the stator rings.

In some embodiments, each stator ring comprises a plurality of curved vanes, each said volute path separated from an adjacent volute path in the stator ring by a said curved vane.

In some embodiments, each stator ring comprises the plurality of curved vanes spaced circumferentially apart radially outside of or adjacent to or at the radial outer perimeter of the impeller or a respective one of a first impeller and a second impeller.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "and/or" means "and" or "or", or both.

As used herein "(s)" following a noun means the plural and/or singular forms of the noun.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION OF PREFERRED EMBODIMENTS

Figure 1:
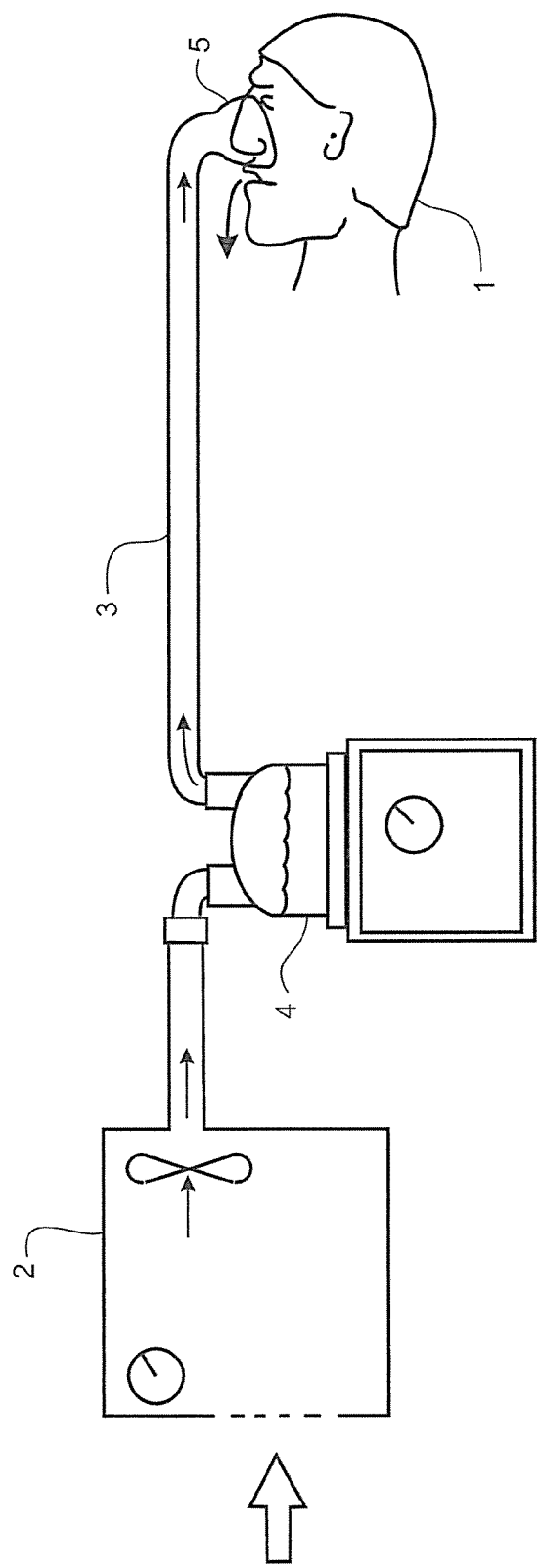
FIG. 1 is a schematic representation of a prior art respiratory system.
Figure 2:
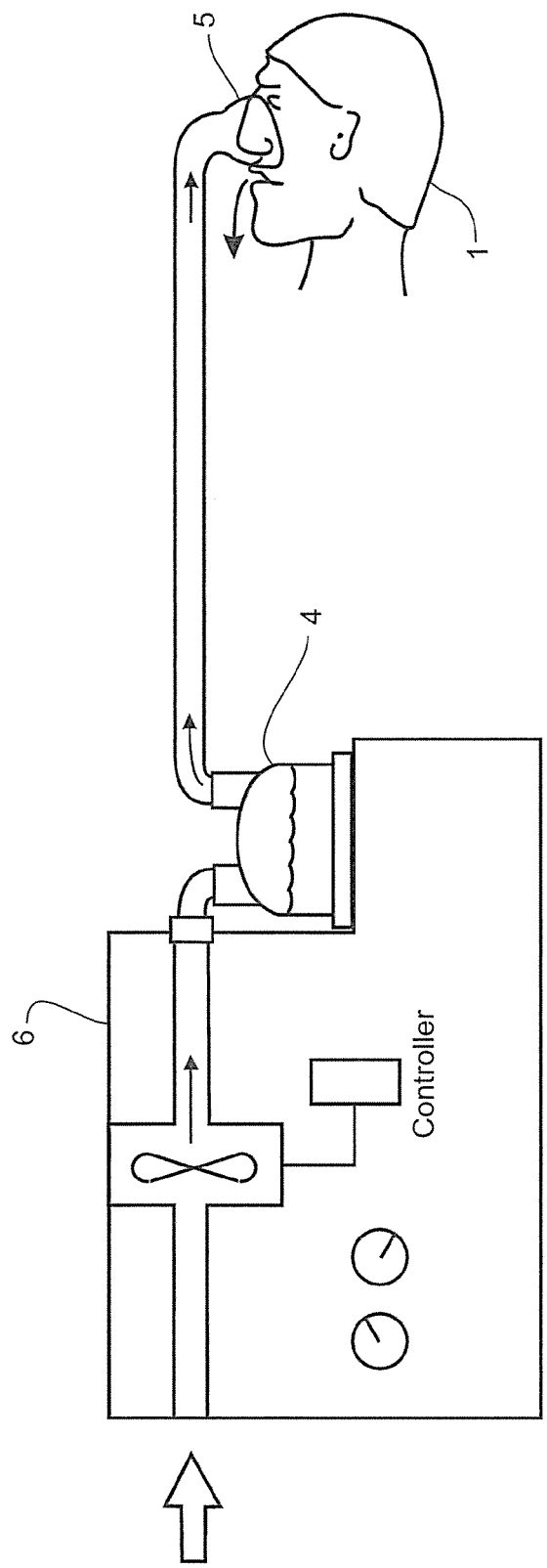
FIG. 2 is a schematic representation of another prior art respiratory system.

Various embodiments are described with reference to the Figures. The same reference numerals are used throughout to designate the same or similar components in various embodiments described.

Figure 12:
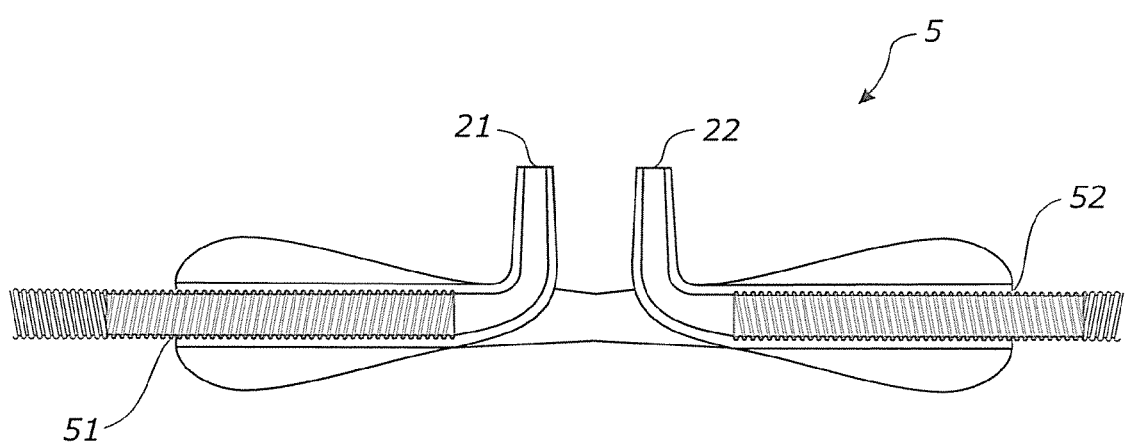
FIG. 12 shows a cross section of a typical cannula that may be used in the respiratory system of FIG. 3.

This present disclosure relates to an improved blower or respiratory system for providing a flow of respiratory gases to a user. In some embodiments the gases are provided to the user via a nasal interface that engages the user's nares. The nasal interface may be a non-sealing or a sealing interface. In some embodiments the nasal interface may be a nasal cannula, or alternatively a nasal interface with nasal pillows that seal against respective nares of the user. In each example, the nasal interface comprises two outlets, each outlet for providing a flow of gases to a corresponding one of the user's two nares. An example nasal interface comprising two outlets is shown in FIG. 12.

One of the nares of a user or patient receiving a flow of respiratory gases from a blower may become occluded or partially occluded, for example by a buildup of mucus in one of the nasal passages of the user. Where one of a patient's nares is blocked or partially blocked, respiratory gases therapy provided by the respiratory system may be less effective than it otherwise would be if both nares of the user were not so blocked or partially blocked. Alternatively, in some instances a user may prefer to breath via the mouth, and in such circumstances it may be beneficial to flush the user's nasal passages with air, or to switch from providing a flow of gases between the user's nares and mouth, for example periodically.

Figure 3:
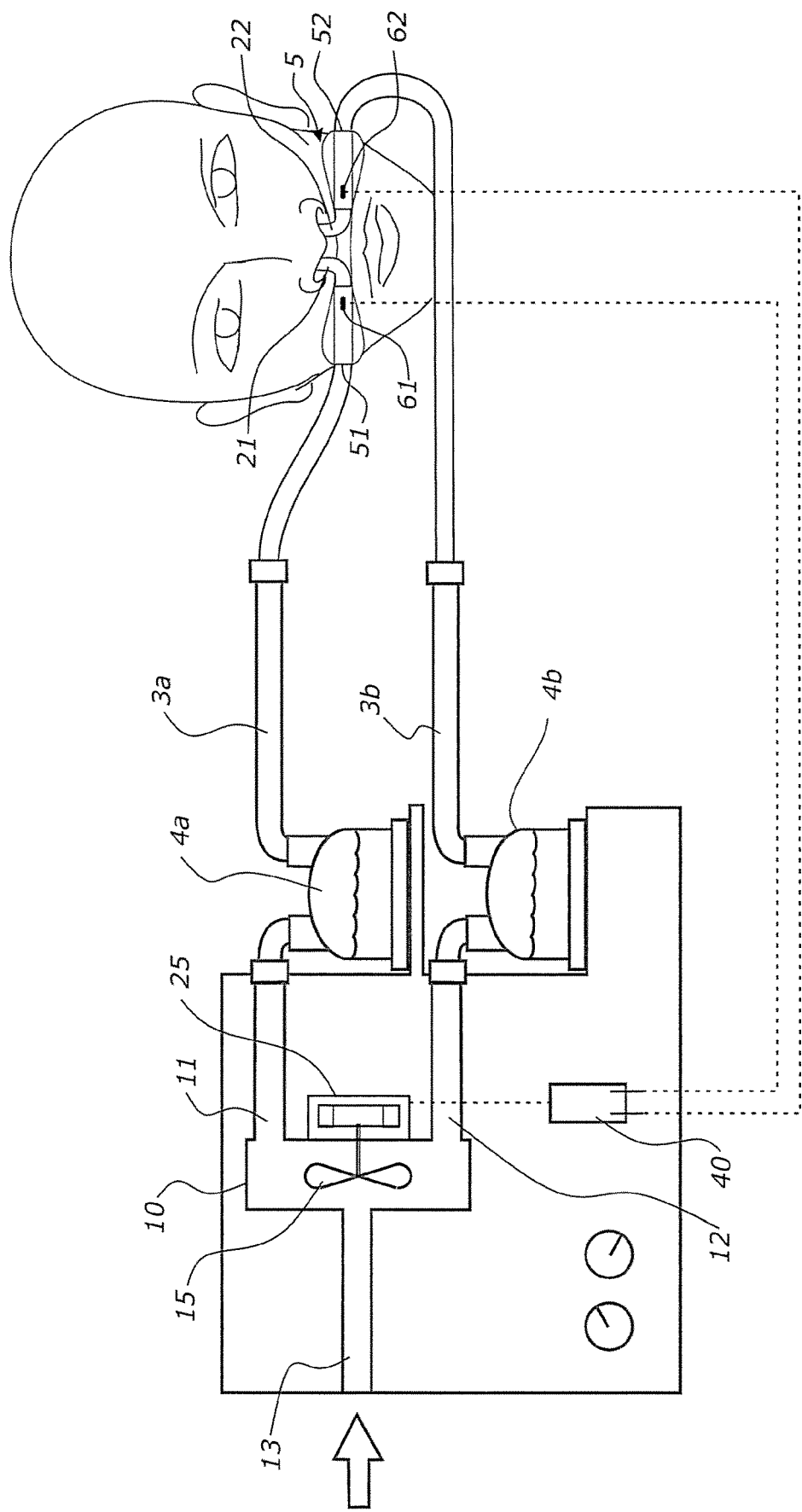
FIG. 3 is a schematic representation of a respiratory system in accordance with at least one of the embodiments disclosed herein.

With reference to the schematic of FIG. 3, a system according to some embodiments comprises a dual outlet blower 10, wherein each outlet 11, 12 provides a flow of gases to one of a pair of nasal outlets 21, 22 of a nasal interface 5.

According to embodiments described herein, the dual outlet blower 10 comprises an impeller 15 and a housing comprising a first outlet 11 and a second outlet 12. The first outlet 11 is arranged to direct a flow of gases from the housing when the impeller rotates in a first direction of rotation, and the second outlet 12 is arranged to direct a flow of gases from the housing when the impeller rotates in an opposite second direction of rotation. The dual outlet blower 10 provides a means to direct a flow of gases to one of the nares of a user or the other one of the nares of a user by simply selecting a direction of rotation of the blower impeller. Where one of the nares of a user becomes blocked or partially blocked, flow may be provided to the other one of the user's nares by selecting a corresponding direction of rotation of the impeller.

Rotation of the impeller is driven by a motor 25. The motor is adapted to rotate the impeller in both of a first direction of rotation and an opposite second direction of rotation. Energizing the motor to rotate the impeller in a first direction of rotation generates a flow of gases to exit the first outlet of the housing. This flow may be directed to a first nasal outlet of a nasal interface. Energizing the motor to rotate the impeller in an opposite second direction of rotation generates a flow of gases to exit the second outlet of the housing. This flow may be directed to a second nasal outlet of the nasal interface.

A system according to embodiments herein comprises a first respiratory system between the first blower outlet 11 and a first outlet 21 of the nasal interface 5, and a second respiratory system between the second blower outlet 12 and a second outlet 22 of the nasal interface 5, wherein the first and second respiratory systems are pneumatically separate. The first and second respiratory systems may each comprise a conduit 3a, 3b extending between the corresponding blower outlet 11, 12 and the corresponding nasal interface outlet 21, 22. In some embodiments, the nasal interface comprises a first inlet 51 in pneumatic communication with the first outlet 21 of the nasal interface via a first lumen, and a second inlet 52 in pneumatic communication with the second outlet 22 of the nasal interface via a second lumen, wherein the first and second lumens are pneumatically separate. A first conduit 3a may extend between the first outlet 11 of the blower and the first inlet 51 of the nasal interface, and a second conduit 3b may extend between the second outlet 12 of the blower and the second inlet 52 of the nasal interface.

In some embodiments, the system may comprise dual humidifiers. For example the first respiratory system between the first blower outlet 12 and the first outlet 21 of the nasal interface may comprise a first humidifier 4a, and the second respiratory system between the second blower outlet 12 and the second outlet 22 of the nasal interface may comprise a second humidifier 4b, as illustrated by the schematic of FIG. 3. Alternatively the system may be without humidification to provide a flow of un-humidified gases to the user. In a further alternative embodiment, a single humidifier may be provided upstream of the blower, to humidify a flow of gases entering the blower via the blower inlet 13.

In some embodiments the respiratory system comprises a sensing arrangement to determine occlusion or partial occlusion of one of the nares of the user and control the direction of rotation of the impeller in response. If the sensing arrangement detects one of the user's nares is at least partially occluded, the sensing arrangement may cause the impeller to rotate in one of the first and second directions of rotation to generate a flow to the other one of the user's nares, and vice versa.

In some embodiments, the sensing arrangement may comprise a pressure or flow sensor to detect a pressure or flow to or at the user's nares to determine if one or other of the user's nares is at least partially occluded. For example, the sensing arrangement may comprise a first pressure or flow sensor 61 to detect a pressure or flow to or at one of the user's nares to determine if the one of the user's nares is at least partially occluded, and a second pressure or flow sensor 62 to detect a pressure or flow to or at the other one of the user's nares to determine if the other one of the user's nares is at least partially occluded. A controller 40 may be provided to receive signals from the sensing arrangement to energise the motor 25 to rotate the impeller in the first or second direction depending on whether one or other of the user's nasal passages is occluded or partially occluded. For example, a pressure or flow sensor may provide a signal to the controller that compares the signal to a threshold, and where the signal indicates the pressure or flow at one of the user's nares is more than or less than a predetermined threshold indicative of one nare being at least partially occluded, the controller may energise the motor to rotate the impeller in one of the first and second rotational directions to cause a flow of gases to be provided to the one of the user's nares that is not occluded. In FIG. 3 the sensors 61, 62 are indicated as being located at the patient interface, however the sensors may be located elsewhere in the system, for example at the outlets 11, 12 of the blower or between the blower outlets and the outlets of the nasal interface.

In some embodiments, a respirator system comprises a dual outlet blower 10, wherein one of the first and second outlets 11, 12 provides a flow of gases to at least one of the user's nares and the other one of the first and second outlets 11, 12 provides a flow of gases to the user's mouth. In some embodiments the respiratory support system comprises an oro-nasal interface. The oro-nasal mask comprises at least one nasal outlet for providing a flow of respiratory gases to a user via at least one of the user's nares, and an oral outlet for providing a flow of respiratory gases to the user via the user's mouth. The first outlet of the blower housing is in fluid communication with the nasal outlet of the oro-nasal interface, and the second outlet of the blower housing is in fluid communication with the oral outlet of the oro-nasal interface. Rotation of the impeller in a first direction of rotation generates a flow of gases to the nasal outlet, and rotation of the impeller in a second direction of rotation generates a flow of gases to the oral outlet. A system may comprise a controller configured to control the direction of rotation of the impeller based on at least one of a user input, a measured condition, or a predetermined condition. For example, the controller may control the impeller to rotate in a direction to provide a flow to the user's mouth and to control the impeller to rotate in an opposite direction periodically to provide a flow to the user's nares, to periodically flush the user's nasal passages.

It is also possible to provide a system comprising a first blower and a separate second blower. In one configuration, the first blower may provide a flow of gases to one of a pair of nasal outlets of a nasal interface, and a second blower may provide a flow of gases to the other one of the pair of nasal outlets of the nasal interface. In another configuration, the first blower may provide a flow of gases to one of a nasal outlet and an oral outlet of an oro-nasal interface, and the second blower may provide a flow of gases to the other one of the nasal outlet and the oral outlet of the oro-nasal interface.

An example of a dual outlet blower suitable for implementation in a system such as those described above is now described with reference to FIGS. 4 to 8. Further alternatives are also described, including a blower described with reference to FIGS. 9 to 11.

Figure 4:
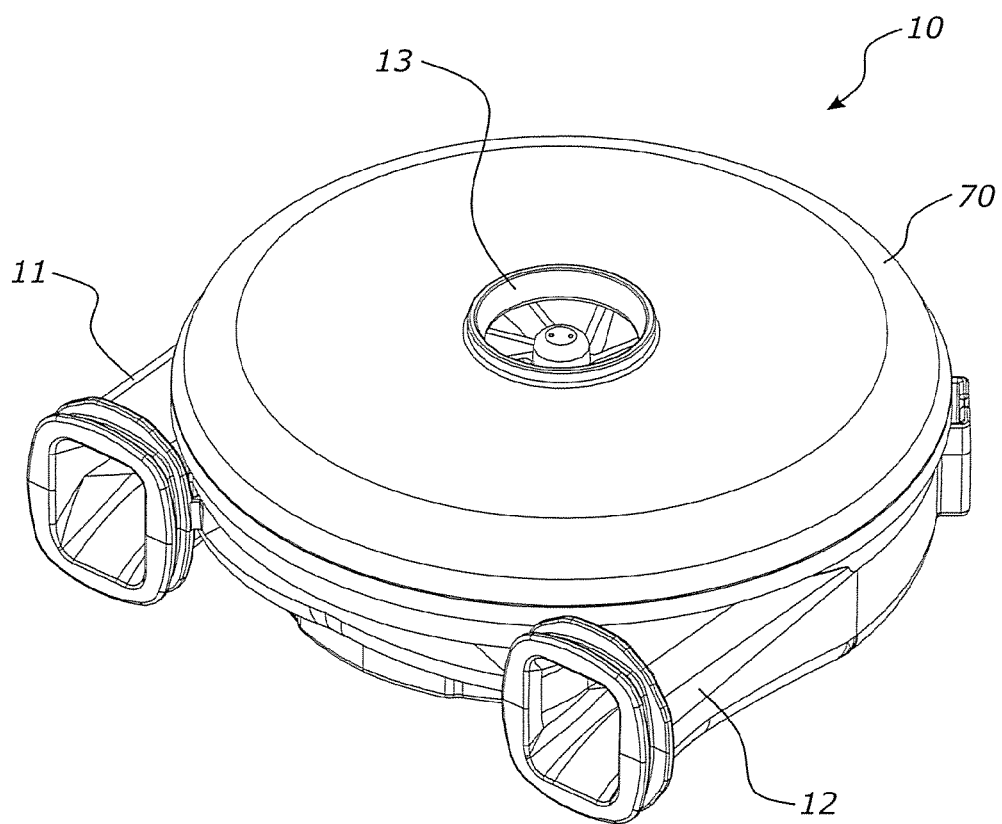
FIG. 4 shows a blower housing for a blower in accordance with at least one of the embodiments disclosed herein.
Figure 5A:
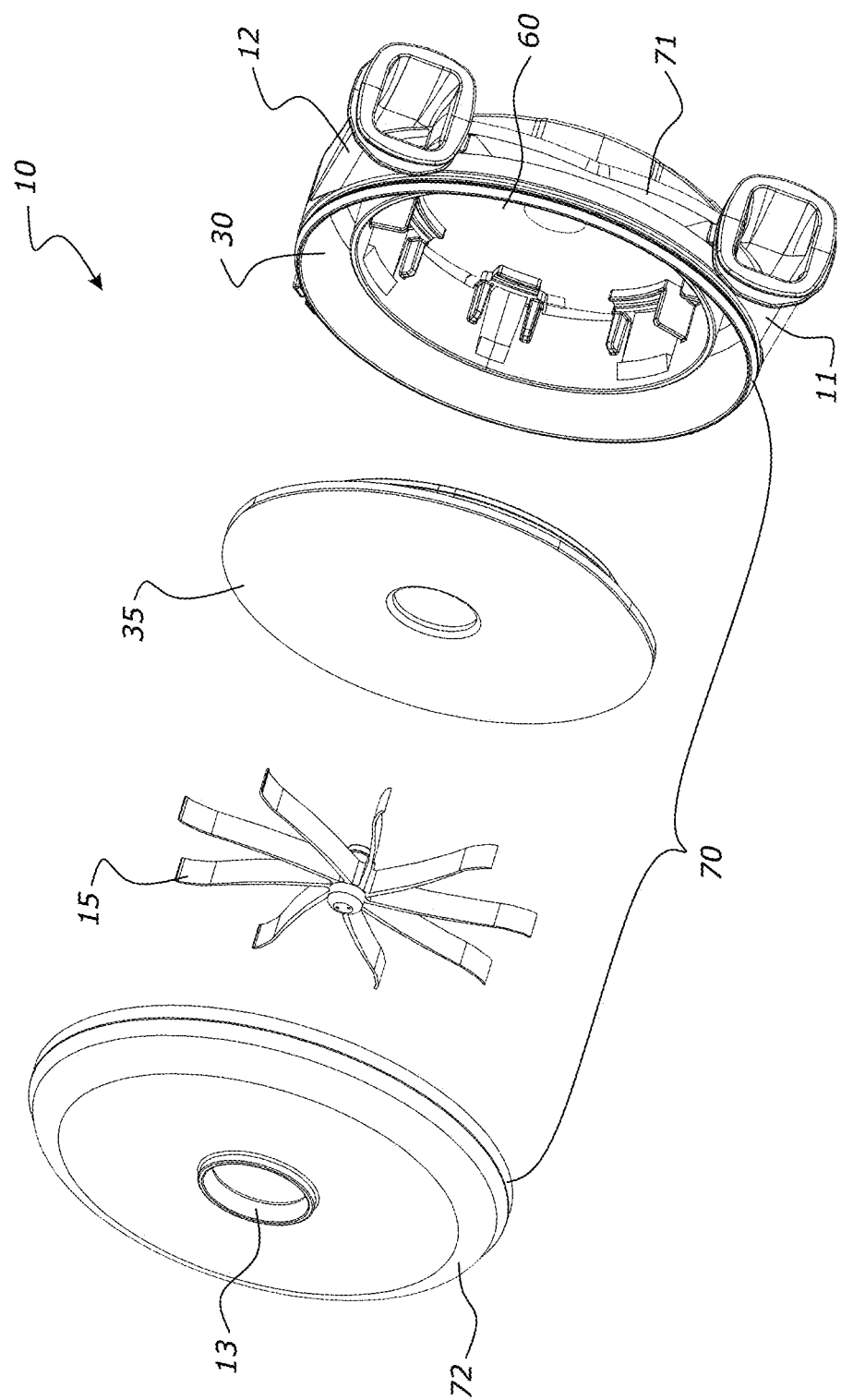
FIGS. 5A and 5B are exploded views of a blower in accordance with at least one of the embodiments disclosed herein, comprising the housing of FIG. 4 but and with a motor omitted from the figure.
Figure 5B:
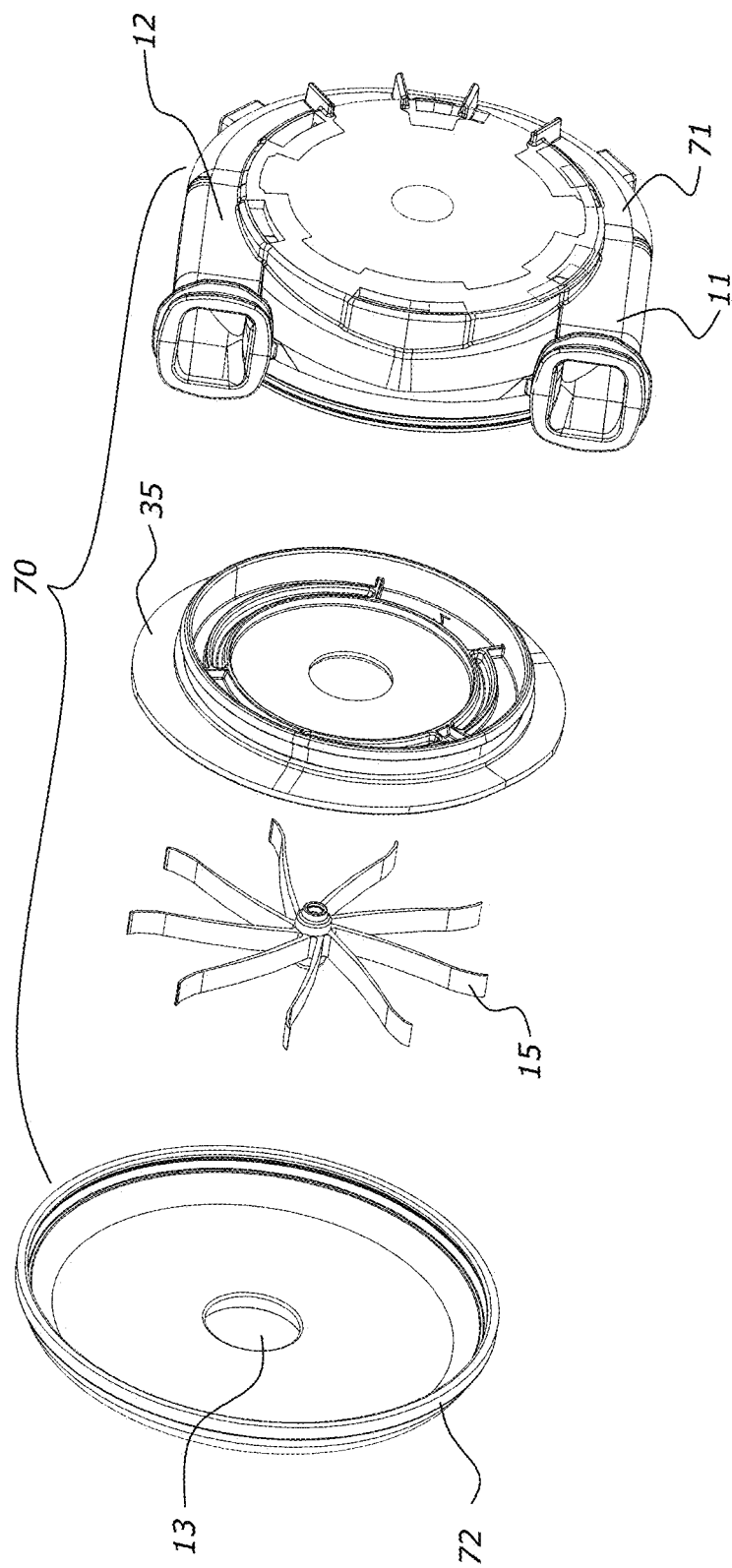

FIG. 4 illustrates a housing 70 of the blower 10. FIGS. 5a and 5b show an exploded view of the blower 10, but with a motor of the blower omitted. A motor that may be suitable for driving the impeller is described in international patent publication WO2013/009193, the contents of which are incorporated herein by reference.

As shown, the blower 10 comprises the impeller 15, and the housing 70. The housing comprises an impeller chamber 20 (FIG. 7) in which the impeller rotates to generate a pressurised flow of gases, and a first outlet 11 and a second outlet 12. The first outlet 11 is arranged to direct a flow of gases from the housing 70 when the impeller rotates in a first direction of rotation illustrated as direction A in FIG. 6, and the second outlet 12 is arranged to direct a flow of gases from the housing 70 when the impeller rotates in an opposite second direction of rotation, illustrated as direction B in FIG. 6.

As shown in FIGS. 5a and 5b, in some embodiments the housing may comprise two or more parts assembled together. In the illustrated embodiment, the housing comprises a first or main housing part 71 and a second housing part or cap 72 that assembles to the first housing part 71. The first housing part 71 may comprise the first and second outlets, and the second housing part or cap 72 may comprise the blower inlet 13.

The first and second inlets 11, 12 each comprise a conduit extending from a volute chamber 30 of the housing 70. Typically a 'volute chamber' in a pump is a curved funnel that increases in area towards an outlet of the pump. However, in this specification and claims, the term 'volute chamber' should be interpreted broadly to mean a housing or chamber that receives air pumped by the impeller from the impeller chamber and in which the velocity of the air flow decreases to cause a relatively higher pressure. Thus the volute chamber of a blower according to embodiments described herein is not necessarily volute-shaped.

Rotation of the impeller within the impeller chamber draws air into the impeller chamber 30 via the inlet 13 of the blower. The inlet 13 is preferably located centrally with respect to a rotational axis of the impeller.

As the impeller rotates in the impeller chamber, the impeller draws air into the impeller chamber from the inlet and forces air from the impeller chamber into the volute chamber via a passage 19 between the impeller chamber 20 and the volute chamber 30. The air collecting in the volute chamber passes from the volute chamber via the first outlet 11 or the second outlet 12, depending on the rotational direction of the impeller.

In the figures the impeller is illustrated as an asymmetric impeller, which is an impeller that is configured to generate more flow when rotating in one direction compared to the opposite direction. For example, in an asymmetric impeller the impeller blades 16 may be angled from the hub 17 of the impeller and/or may be curved or otherwise shaped for the impeller to be preferentially rotated in one direction. However, in other embodiments the impeller may be a symmetrical impeller, for example configured with radially extending blades that are straight or otherwise shaped to give a given flow rate for a given rotational speed regardless of rotational direction.

Figure 6:
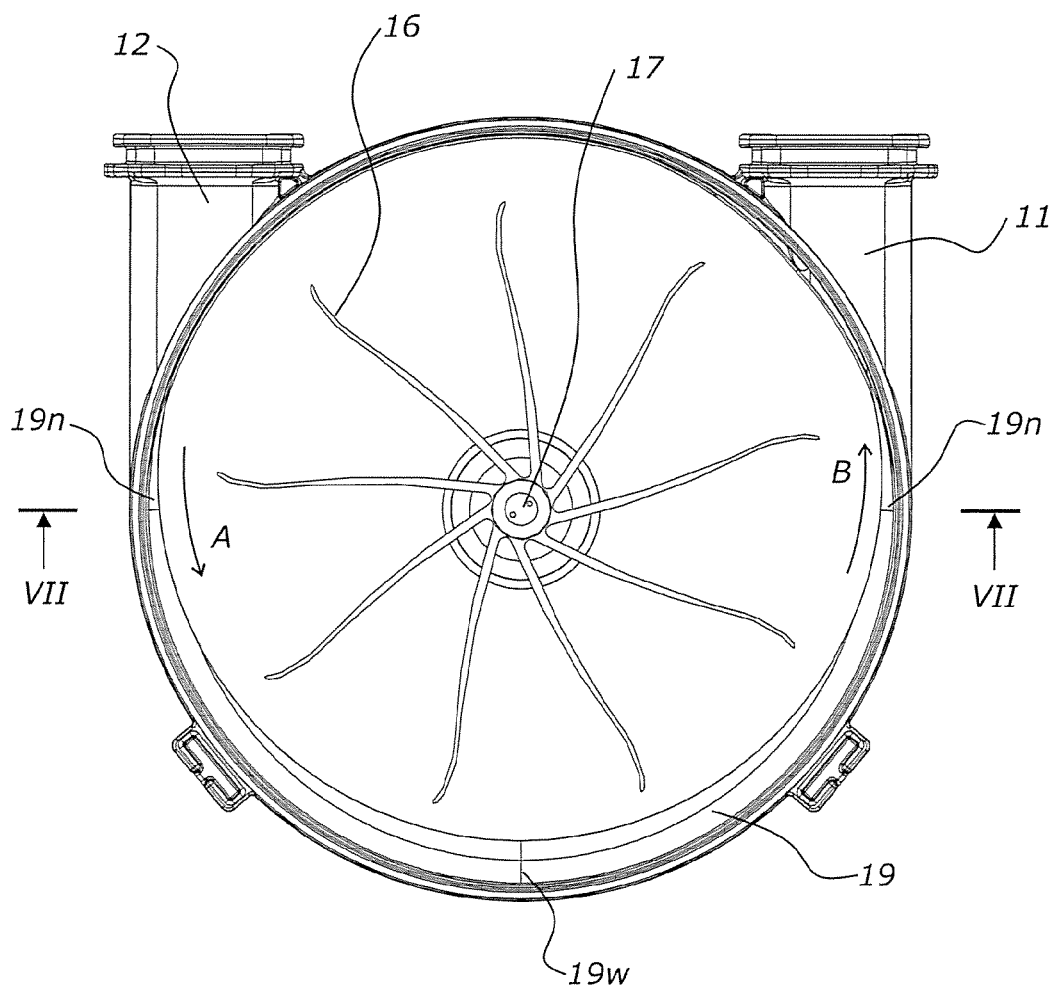
FIG. 6 is shows the blower of FIGS. 5A and 5B with part of the housing removed to show an end view of an impeller of the blower.
Figure 7:
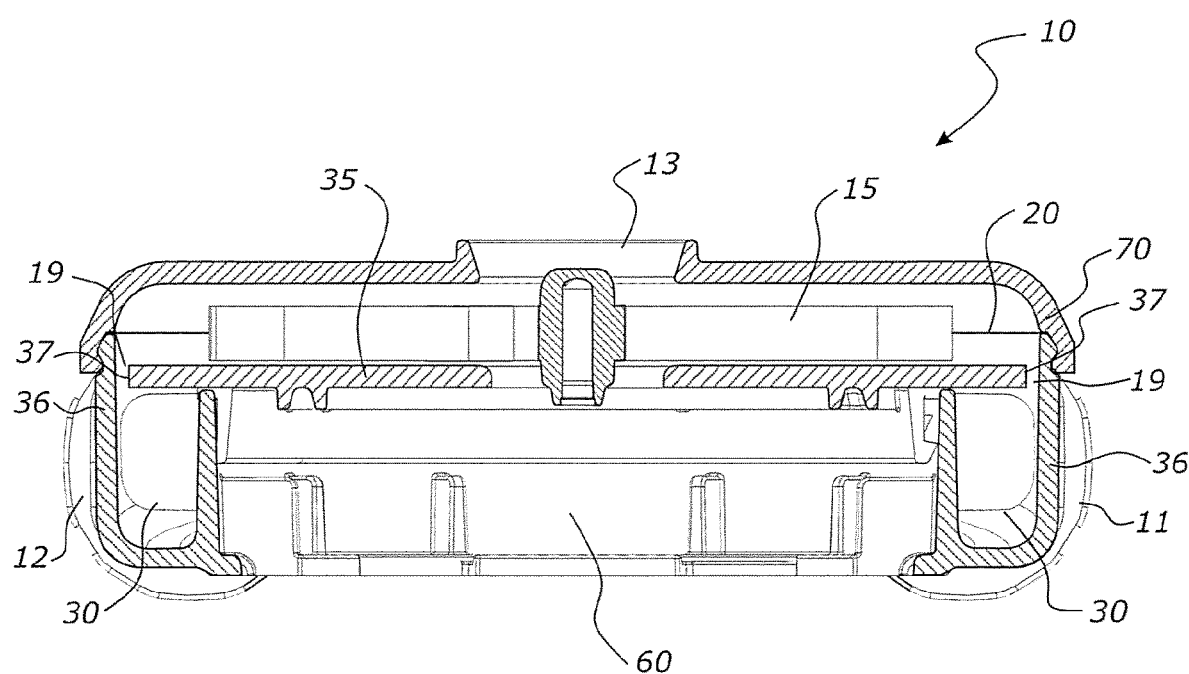
FIG. 7 shows a cross section of the blower of FIGS. 5A and 5B on line IIX-IIX in FIG. 6.
Figure 8:
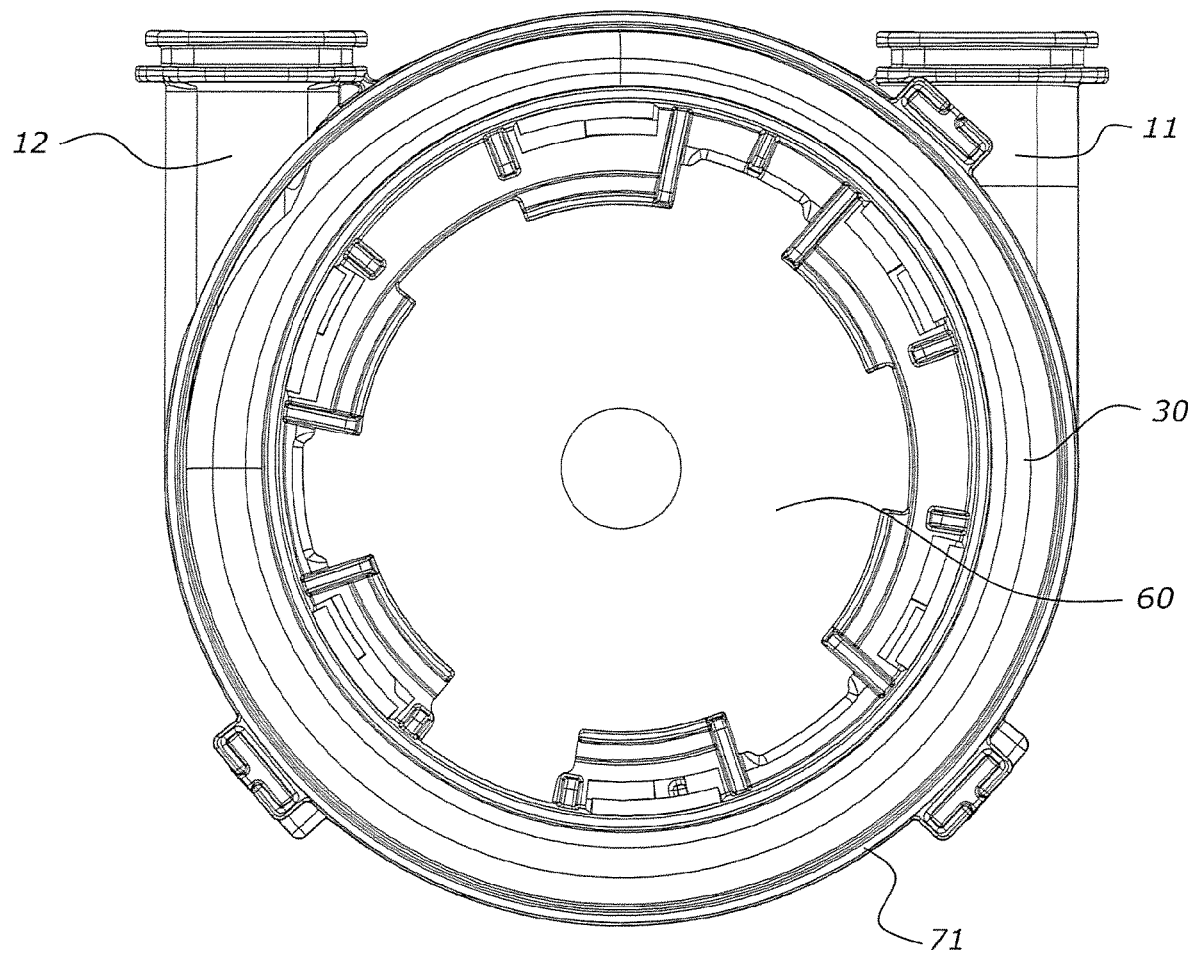
FIG. 8 shows a cross sectional view of the blower housing of FIG. 4 showing a volute chamber and motor chamber of the housing.

In some embodiments the impeller chamber 20 and the volute chamber 30 are separated by a dividing wall. In some embodiments the impeller chamber is separated from the volute chamber by a dividing wall 35 of the housing 70. In some embodiments the passage 19 between the impeller chamber 20 and the volute chamber 30 is an aperture in the dividing wall. As shown, in some embodiments the dividing wall does not extend fully to a side wall 36 of the volute chamber, and the passage is a gap 19 between an edge 37 of the dividing wall 35 and the side wall 36. The side wall may be a circumferential side wall of the blower housing. In some embodiments the passage 19 is crescent shaped. In some embodiments, the gap 19 between the dividing wall and the side wall is crescent shaped. For example, as best shown in FIG. 6, the gap 19 is crescent shaped, tapering on either side of a widest point 19w of the passage to a narrow point or narrow points 19n either side of the widest point. Preferably the widest point 19w is located midway between the first and second outlets 11, 12, as shown in FIG. 6. The passage 19 between the impeller chamber and the volute chamber is radially outside the blower inlet 13. In an embodiment wherein the passage 19 is an aperture in the wall 35, preferably the aperture is adjacent to a side wall of the housing. Further, preferably the aperture is midway between the first and second outlets.

In some embodiments, the first and second outlets 11, 12 extend tangentially or substantially tangentially from the volute chamber. For example, the outlets may extend from the housing at an angle of less than 30 degrees, or less than 20 degrees, or less than 10 degrees from a tangent to the rotational axis of the impeller. In some embodiments, the first outlet 11 extends substantially tangentially from the housing with respect to a first direction of rotation of the impeller, and the second outlet 12 extends substantially tangentially from the housing with respect to an opposite second direction of rotation of the impeller. For example, as shown in FIG. 6, the first and second outlets are positioned to be mirror images of one another on a centreline of the housing or a line extending through the rotational axis of the impeller, such that the outlets are parallel and with both extending in a single lateral direction. Other arrangements are possible, for example the first and second outlets 11, 12 may extend from the housing to be at a right angle or 90 degrees to one another. In yet another alternative, the outlets may be in-line and extending in opposite lateral directions. For example, with reference to FIG. 6 in which the first and second outlets 11, 12 extends downwards, in some embodiments the first outlet 11 may extend downwards and the second outlet 12 may extend upwards and in line with the first outlet. As illustrated in the Figures, the impeller is a centrifugal impeller. A centrifugal impeller generates a flow velocity that may be resolved into a tangential component of velocity and a radial component of velocity. In some embodiments, the first outlet is arranged to extend from the housing to receive at least a substantial portion of a tangential component of velocity of air flow generated by the impeller when rotating in a first direction of rotation, and the second outlet is arranged to extend from the housing to receive at least a substantial portion of a tangential component of velocity of air flow generated by the impeller when rotating in a second direction of rotation. Thus, by simply changing direction of rotation of the impeller by changing direction of the motor rotation, air flow may be directed predominantly from either the first outlet or the second outlet of the housing. The blower arrangement is configured to provide flow to a selected outlet and therefore a selected one of the nares of a user or a selected one of the user's nose and mouth, by motor direction control and without the requirement for other devices such as valves and valve actuation devices.

In some embodiments, rotation of the impeller in a first direction of rotation generates a first flow of gases from the first outlet and a second flow of gases from the second outlet, wherein the first flow of gases is greater than the second flow of gases. In an embodiment where the flow paths from the impeller to the first and second outlets are equivalent and the impeller is symmetrical, rotation of the impeller in the opposite second direction of rotation generates the first flow of gases from the second outlet and the second flow of gases from the first outlet. In other words, in the first direction of rotation a particular flow rate is provided via the first outlet, and in the second direction of rotation the same flow rate is provided by the second outlet, for a given impeller speed. Alternatively, for example where the impeller is asymmetrical, rotation of the impeller in a first direction of rotation generates a first flow of gases from the first outlet and a second flow of gases from the second outlet, and rotation of the impeller in an opposite second direction of rotation generates a third flow of gases from the second outlet and a fourth flow of gases from the first outlet, wherein the flow rate of the first flow of gases is greater than the flow rate of the second flow of gases, and the flow rate of the third flow of gases is greater than the flow rate of the fourth flow of gases. For a symmetrical blower configuration the third flow rate is substantially equal to the first flow rate, and the fourth flow rate is substantially equal to the second flow rate.

In some embodiments the housing 10 provides a motor chamber 60, for housing the motor within the housing of the blower. In some embodiments the volute chamber 30 extends around the motor chamber 60. In other words, the motor is located radially inside of the annular volute chamber 30. In some embodiments the motor is located radially inside of the annular volute chamber. An aperture is provided between the motor chamber and the impeller chamber so that a shaft of the motor or impeller can extend between the impeller and the motor to rotationally couple the impeller to the motor. Positioning the motor radially inside of the annular volute achieves a flat (small axial length) blower configuration.

In some embodiments the blower may comprise one or more electronic circuit boards, for example the blower may include motor control electronics. In some embodiments, the electronics may be provided remotely from the blower. In such an embodiment, a cable to the blower may provide communications and motor control current and/or voltage from a remote motor controller to the motor.

A table of flow performance data for the blower illustrated in FIG. 4 is provided below. Blocked flow indicates pressure generated at the blower outlets 11, 12 with the outlets blocked. Bias resistance flow is the flow that vents from the patient interface (e.g. nasal cannula 5 in FIG. 3) when the outlets from the interface are blocked. For example, there is a leak at the interface with a resistance that vents approximately 30 to 40 lpm at 10cmH$_2$O. Bias flow is the minimum leak in the respiratory system independent of inhalation and exhalation by the patient. Open flow is the flow rate that is achieved at the outlets 11, 12 with no downstream flow resistance.

|  | Impeller speed (rpm) | Pressure 1 (cmH2O) | Pressure 2 (cmH2O) | Flow 1 (lpm) | Flow 2 (lpm) |
| --- | --- | --- | --- | --- | --- |
| Blocked flow | 10K | 12 | 11 | 0 | 0 |
| Bias resistance | 10K | 10 | 7 | 33 | 27 |
| Open flow | 10K | 2.6 | 0.1 | 130 | 26 |
| Blocked flow | 20K | 25 | 23 | 0 | 0 |
| Bias resistance | 20K | 20 | 14 | 47 | 38 |
| Open flow | 20K | 4.6 | 0.2 | 190 | 36 |

As shown in the table, for open flow with the impeller rotating in one direction, the flow rate from one outlet is about 20% of the flow from the other outlet. However, this significant difference in flow from the two outlets is not experienced in practice. For bias flow, the flow rate from one outlet is about 80% of the flow from the other outlet. In normal operation, during exhalation the blower provides a flow in the range of between blocked flow (no flow) and bias flow, and during inspiration the peak flow provided by the blower including bias flow may be approximately 80 lpm at 10K rpm. Thus in normal operation during inspiration, the flow rate from one outlet may be approximately one third of the flow from the other outlet.

Figure 9:
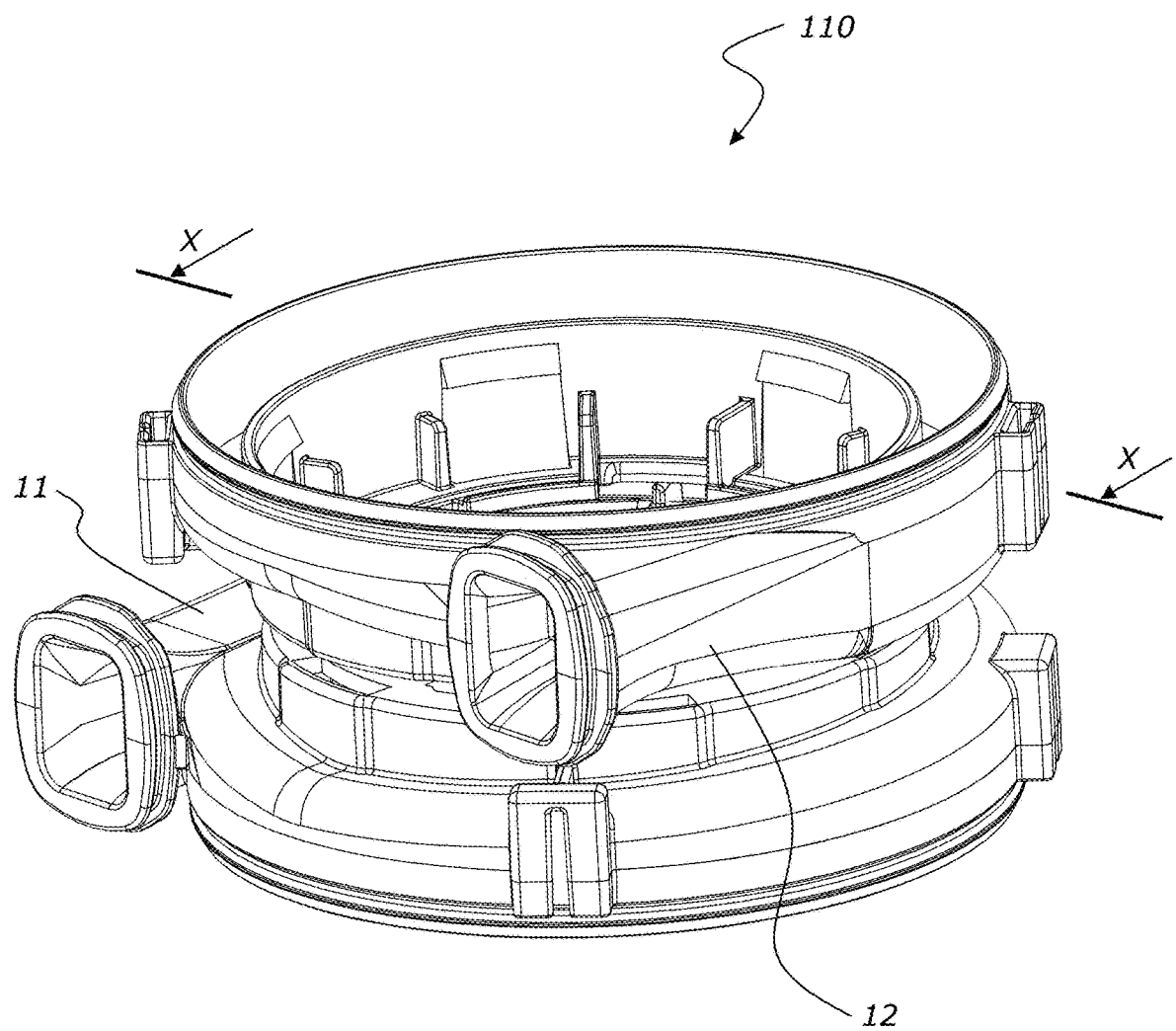
FIG. 9 shows an alternative blower housing for a blower in accordance with at least one of the embodiments disclosed herein.
Figure 10:
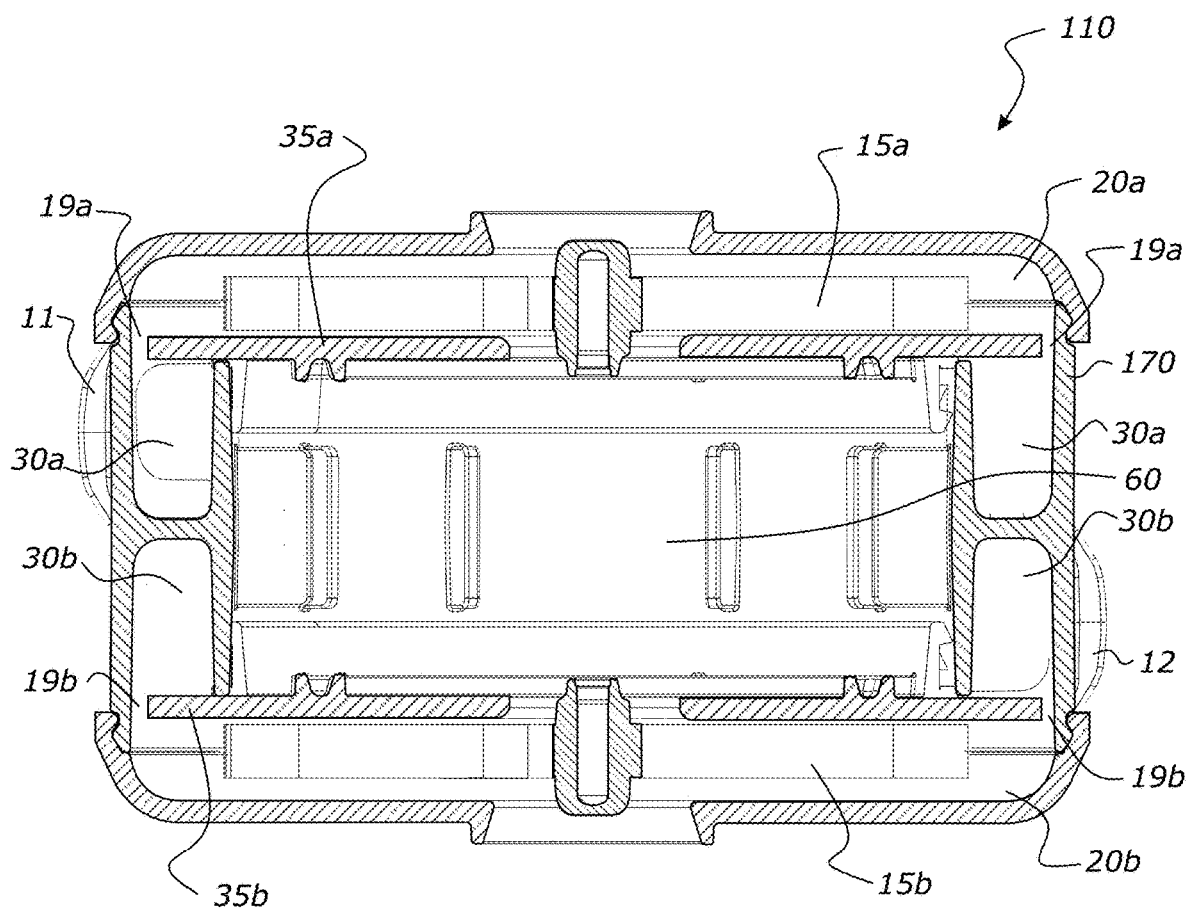
FIG. 10 shows a cross section of a blower in accordance with at least one of the embodiments disclosed herein comprising the housing of FIG. 9, the cross section on line X-X in FIG. 9.

An alternative blower 110 is described with reference to FIGS. 9 to 11. An alternative housing 170 is illustrated in FIG. 9, and a cross section of the blower 110 with motor omitted is shown in FIG. 10. A blower comprising the housing of FIG. 9 comprises two impellers 15a and 15b, as illustrated in FIG. 10. The two impellers are axially spaced apart. The housing 170 comprises a first impeller chamber 20a for receiving a first impeller 15a, and a second impeller chamber 20b for receiving a second impeller 15b. A first dividing wall 35a separates the first impeller chamber 20a from a first volute chamber 30a. A second dividing wall 35b separates the second impeller chamber 20b from a second volute chamber 30b. In some embodiments the housing 170 may comprise a single volute chamber that receives a flow of gases from both of the first and second impeller chambers. Each impeller chamber communicates with the volute chambers or chamber via an aperture or gap 19a, 19b as described with reference to the embodiment of FIGS. 4 to 8. In the embodiment of FIGS. 9 and 10, the housing comprises a single motor chamber 60. A motor comprising a stator and rotor is located in the motor chamber. The motor chamber and motor are located axially between the first impeller chamber and the second impeller chamber. The rotor is coupled to the first and second impellers 15a and 15b, so that the rotor and the first and second impellers rotate together. In a first direction of rotation the first impeller generates a flow of gases to exit the first volute chamber or the volute chamber via the first outlet 11. In a second direction of rotation the second impeller generates a flow of gases to exit the second volute chamber or the volute chamber via the second outlet 12.

Figure 11:
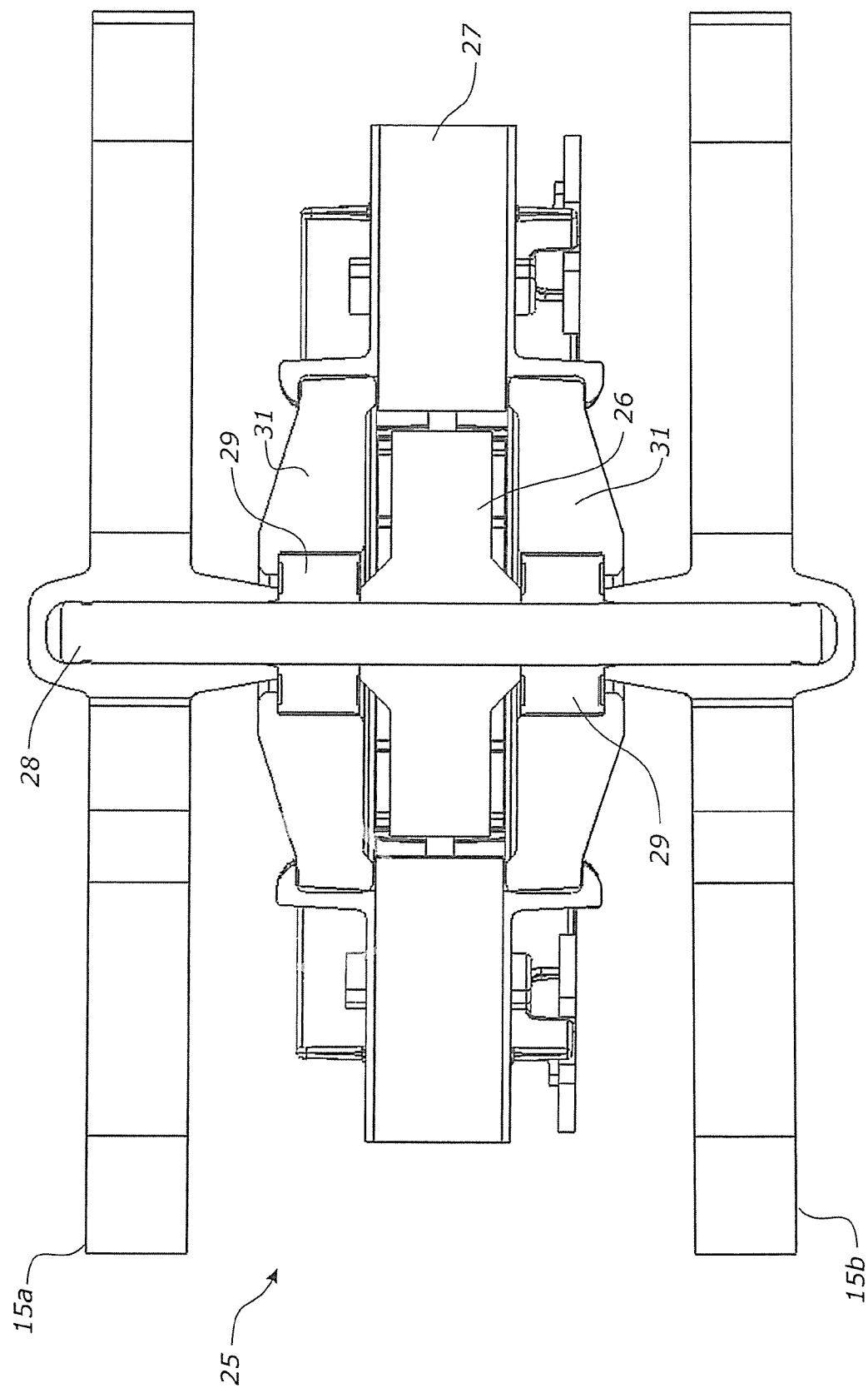
FIG. 11 shows a cross section of a motor configuration suitable for use in the blower of FIG. 10.

An example rotor and dual impeller configuration for use in the blower 110 is shown in FIG. 11. The motor 25 comprises a rotor 26 coupled to the first and second impellers 15a, 15b by a shaft 28. The rotor is positioned inside stator 27 and supported by bearing elements 29 to rotate relative to the stator 27. The bearing elements are supported by bearing mounts 31. The bearing mounts may be resilient, for example formed from an elastomer. In the illustrated embodiment the bearing elements are supported by the bearing mounts 31 located between the stator and the bearing elements, with the bearing elements located on the shaft. The stator is supported in the motor chamber 60 of the blower housing 170. A resilient mount may be provided to mount the stator within the motor chamber 60. A similar motor and impeller arrangement may be utilized in the blower 10 described with reference to FIGS. 4 to 8, but with a single impeller coupled to a shaft 27 extending from one end of the motor.

The blowers illustrated in FIGS. 4 to 8 and in FIGS. 9 and 10 are centrifugal blowers, comprising a centrifugal impeller (or impellers) with a housing to generate tangential air flows. However, in other embodiments, a dual outlet blower may comprise an impeller or impellers and a housing to generate axial air flows. In some embodiments, a blower comprising an impeller comprises a first axial outlet at a first side of the blower and a second axial outlet at a second side of the blower. In a first direction of rotation the impeller generates a flow of gases to exit the first axial outlet of the housing. In a second direction of rotation the impeller generates a flow of gases to exit the second axial outlet of the housing. In some embodiments the blower comprises a housing with a first impeller chamber for receiving a first impeller, and a second impeller chamber for receiving a second impeller, and a first axial outlet associated with the first impeller chamber and a second axial outlet associated with the second impeller chamber. The housing may also comprise a single motor chamber. A motor comprising a stator and rotor is located in the motor chamber. The motor chamber and motor may be located axially between the first impeller chamber and the second impeller chamber. The axial blower may comprise a dual impeller and rotor configuration like the configuration shown in FIG. 12, wherein the rotor is coupled to the first and second impellers, so that the rotor and the first and second impellers rotate together. In a first direction of rotation the first impeller generates a flow of gases to exit the first axial outlet of the housing. In a second direction of rotation the second impeller generates a flow of gases to exit the second axial outlet of the housing. The impeller or impellers may be centrifugal impellers.

An example dual axial outlet blower is described with reference to FIGS. 13 to 19. The blower 210 comprises a housing 270. The housing may comprise a first housing part 271 and a second housing part 272. The housing comprises a first wall 273 and a second wall 274 axially spaced apart by a circumferential wall 275. The first and second walls and the circumferential wall combine to form an impeller chamber 20 for receiving the impeller 215. The first and second walls are preferably planar and perpendicular to a rotational axis of an impeller of the blower. In the illustrated embodiment the first and second walls are annular.

The housing further comprises a first central hub 276 and a second central hub 277. In some embodiments, the first central hub 276 is connected via radial ribs 278 to an inner perimeter of the first annular wall 273. In some embodiments, the second central hub 277 is connected via ribs 279 to an inner perimeter of the second annular wall 274. Preferably the ribs connecting each hub to the respective annular wall extend radially between the hub and annular wall.

In some embodiments, the radial ribs 278 extending between the first annular wall 273 and the first central hub 276 comprise an axial extending portion 278a and a radial extending portion 278b, so that the first central hub 276 is axially spaced from the first annular wall 273 and axially away from the impeller chamber 20. This forms a recessed region defined by the first central hub 276 and the ribs 278 extending between the first central hub and the first annular wall. The recessed region forms a motor chamber 60 for receiving a motor 225 comprising a stator 227 and rotor 226. The first hub 276 acts as a support for the stator, and at least a partial support for a first bearing 229, which in turn provides support for the rotor 226 and an impeller 215 assembly. Apertures or gaps 213 between ribs 278 provide a first axial inlet 213. This provides motor cooling also.

The second central hub 277 provides at least a partial support for a second bearing, which in turn also provides support for the rotor 226 and an impeller 215 assembly. In some embodiments, apertures or gaps 214 between ribs 279 provide a second axial inlet 214.

The motor 225 comprises the stator 227 and rotor 226. The stator is supported by the radial ribs 278 and is located radially by the axial portions 278a of the ribs and axially by the radial portions 278b of the ribs. The stator 227 comprises an annular stacked laminated core 227a with a toroidal winding 227b. The rotor comprises an annular or toroidal magnet 226a coupled to a shaft 228. The lower end of the shaft has an annular rebate 228a with an external diameter commensurate with the inner diameter of the annular magnet 226a for receiving the annular magnet. The shaft 228 may be a cylindrical tube in the form of a bearing tube. A bearing e.g. 229 is disposed in the bearing tube at each end. Each bearing may comprise an outer annular bearing race/housing, an inner annular bearing race/housing and ball or roller bearings movable therebetween. As one non-limiting example, the bearings can have an outside diameter of about 4 mm to 8 mm, an inside diameter of about 1.5 mm to 3 mm and a thickness of about 2 mm to 4 mm.

The outer bearing race rotates relative to the inner bearing race. The inner bearing race can remain stationary. In alternatives, a plane bearing or bushing could be used instead. The shaft 228 is supported between the first and second central hubs. Both the first and second housing parts comprise stub axles 269a, 269b extending from the central hub in the form of compliant and/or resilient protrusions that extend into and couple to the respective bearing at each end of the shaft. The protrusions extend into and couple to the bearing race of the respective bearing. Preferably the stub axles are formed from an elastomer (e.g. silicone) or other compliant and/or resilient material, and have a friction fit within the respective bearing races. Alternatively, the stub axles could be solid and/or rigid and are over-moulded with a resilient and/or flexible material. Alternatively, the stub axles could be solid. The stub axle/bearing arrangement enables the shaft to be rotatably supported/coupled in a simply supported manner to the first and second hubs.

The outer diameter of the outer bearing race could be about 4 mm, for example. The hollow shaft could have a commensurate diameter of about 4 mm to allow for a snug fit of the bearing race. The outer shaft size in the rebate 228a could be about 5 mm.

The impeller 215 can be coupled onto (e.g. press fit) or integrally formed with the shaft 228. The shaft can be of similar diameter to the shaft in traditional topologies, which allows for robust mechanical coupling of the impeller. Because the bearings are fitted on the inside of the shaft, the diameter of the shaft is not dictated by the inner diameter of the bearings. The outer diameter of the shaft can then be a suitable size to allow for a robust impeller coupling, e.g. about 5 mm, or alternatively from about 3 mm to about 5 mm. A larger diameter shaft can still be used without dictating the bearing diameter size (leading to undesirably high bearing speeds), because the bearings are internal to the shaft, the size of the bearing (e.g. the diameter size) can be selected based on acceptable bearing speed.

Similarly, the magnet/rotor 226a/226 is pressed into the shaft. Similar advantages apply here, where the shaft can be a suitable size to allow for robust coupling.

Figure 17:
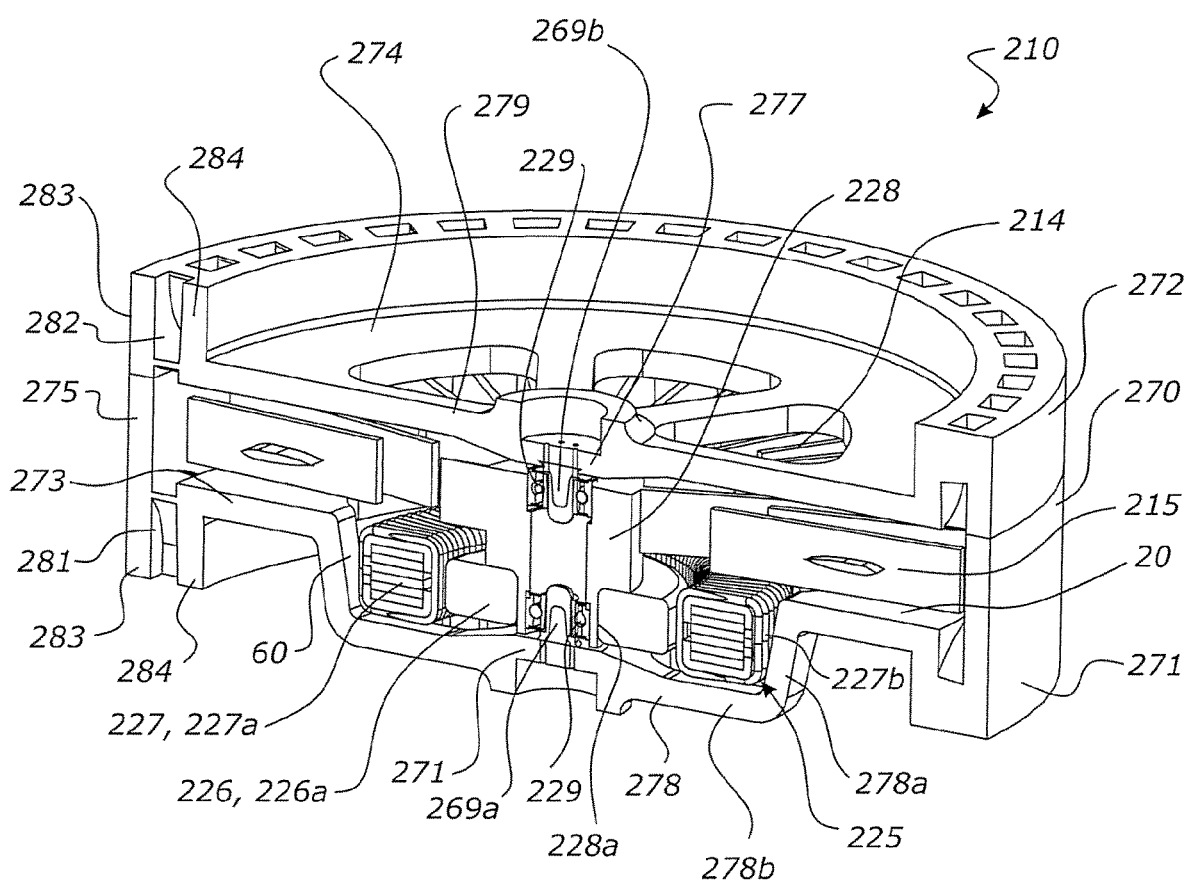
FIG. 17 shows a section view of the blower of FIG. 13 with a section plane through a centre of the blower.
Figure 18:
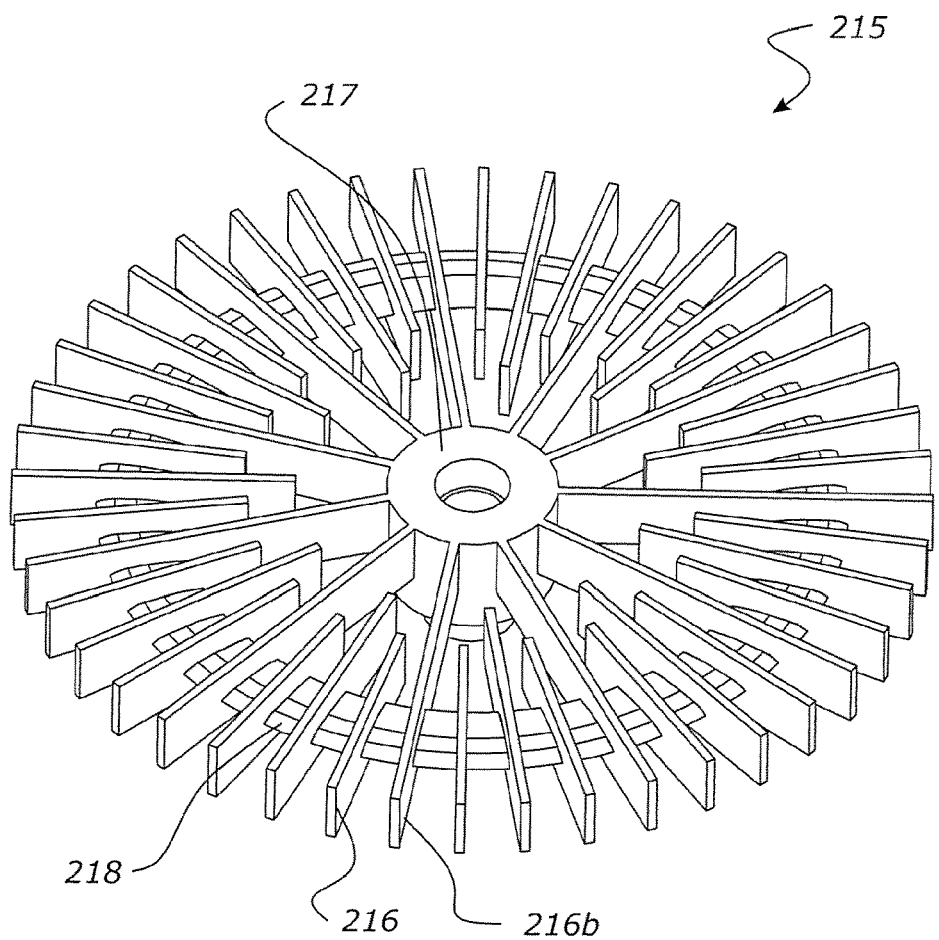
FIG. 18 shows an impeller of the blower of FIG. 13.

The impeller 215 comprises a hub portion 217 and (full-length) blades (sometimes called "vanes") 216, which radially extend from and connect to the hub portion. In the illustrated embodiment the blades extend radially from the hub, but other arrangements may be possible, for example the blades may be angled forward in relation to a direction of rotation of the impeller. The blades may be flat or straight, or the blades may be curved. An annular rib/ring 218 extends between the full length blades to provide rigidity towards the perimeter of the blades. The ring may taper in thickness towards outer and inner radial edges, as shown in FIG. 17. A plurality of short stub (partial-length) blades 216b (also termed "splitter blades") that extend part-way to the hub are interspaced between the full length blades 216. The annular rib 218 also extends between the stub blades 216b, thus supporting them from the full length blades. The stub blades provide additional pressure normally achieved with additional blades, without the requirement for material to extend to the hub which reduces air space at the hub. Reducing airspace at hub reduces the maximum flow capability of the blower 210. If the number of blades is too high (and therefore there is too little air space at the hub due to too many blades), inlet flow is occluded, which restricts the outlet airflow of the blower.

Material properties and construction techniques dictate that it is advantageous to increase the blade count when pumping liquids because of their higher density. For example, the rotation rate (Hz) is multiplied by the number of blades to determine the blade pass frequency. Human hearing is sensitive to tonal inputs between 300 Hz and 15 kHz and if not melodious, it is classified as noise. High frequency sound waves are easier to attenuate than low frequency noise. Typical CPAP blowers have rotational speeds of around 180 revolutions per second. It is therefore advantageous to increase the blade count to improve attenuation characteristics. Unequal, dissimilar and prime numbers like 7, 11, 13, 17, 19 and 23 help to reduce common fraction interactions between rotor and stator. As another example, decelerating a fluid by increasing the flow area rapidly can result in boundary layer separation, flow reversals and turbulent losses. Pressure loss recovery via diffusion mechanisms dictate that the angle between blades should not exceed 12 degrees. Dividing the full circumference (360 degrees) by the sum of the blade thickness angle and the flow channel angle, a minimum blade number for optimal diffusion can be calculated. Adding more blades than optimal reduces the flow channel size with an increase in pressure drop.

But, increasing the blade count to distribute the force that a single blade has to support and to aid noise reduction decreases the size of the flow channel through the impeller, which is disadvantageous. The present inventors have overcome this issue by using stub/splitter blades. To minimise occlusion closer to the hub some blades may be truncated, referred to as splitter blades. Splitter blades could be placed on a support disc or shrouds to transfer their part of the load to the hub. But, blisks (bladed disks) and shrouded impellers have much higher rotational inertia. The present inventors have avoided this by supporting the splitter blades on a rib 218 as described, which reduces inertia over a shroud or disc, and also minimises occlusion.

The housing comprises a first stator ring 281 that encircles the first wall 273, and a second stator ring 282 that encircles the second wall 274. Each stator ring comprises an outer circumferential wall 283 and an inner circumferential wall 284. As shown in the Figures, in some embodiments the outer circumferential wall of the first and/or second stator ring extends axially from the stator ring to form the circumferential wall 275 of the impeller chamber 20. In the illustrated embodiment, the circumferential wall 275 of the impeller chamber is integrally formed with and extends axially from the outer circumferential wall 283 of the first stator ring. The outer circumferential wall 284 of the second stator ring 282 of the second housing part 272 abuts the circumferential wall 275 of the impeller housing 20 of the first housing part 271. The first and second housing parts 271, 272 may be held together by way of bayonets, bumps, snap fits, glue, ultrasonic or friction welding, or any other suitable means. A stator ring is a stationary ring of flow paths.

In each of the first and second stator rings 281, 282, curved channels e.g. 285, 286 (see FIG. 16) are formed between the inner and outer circumferential walls 283, 284 for receiving and slowing airflow from the impeller 215 to create pressure. Thus, rather than a volute chamber like in the earlier described embodiments, in the axial outlet embodiment of FIGS. 13 to 19, each of the first and second stator rings 281, 282 provide a ring of small volute chambers or volute paths 285, 286 spaced apart circumferentially in a ring. The volute paths 285, 286 are located radially outside of the impeller 215 or are located adjacent to or at the radial outer perimeter of the impeller blades 216, 216b of the impeller.

The first and second stator rings 281, 282 provide first and second axial outlets 285, 286. The volute paths 285, 286 of the first and second stator rings 281, 282 provide the first and second axial outlets. Thus each of the first and second axial outlets comprises a plurality of outlet paths, each outlet path being a volute path. A volute path has an increasing area perpendicular to the air flow direction at least part way through the volute path so that the speed of the air flow decreases along the volute path to increase pressure of the flow. For example, the circumferential or radial width or both may increase in dimension from the impeller chamber end of the volute path to the outlet end of the volute path.

The volute paths 285 of the first stator ring 281 are arranged to receive a larger portion of a tangential component of velocity of air flow from the impeller 215 when rotating in a first direction of rotation, compared to the volute paths 286 of the second stator ring 282. And with the impeller rotating in a second opposite direction of rotation, the volute paths 286 of the second stator ring 282 are arranged to receive a larger portion of a tangential component of velocity of air flow from the impeller 215, compared to the volute paths 285 of the first stator ring 281. In some embodiments, the volute paths 285 of the first stator ring 281 extend from the impeller chamber 20 to receive at least a substantial portion of a tangential component of velocity of air flow generated by the impeller 215 when rotating in a first direction of rotation, and the volute paths 286 of the second stator ring 282 extend from the impeller chamber 20 to receive at least a substantial portion of a tangential component of velocity of air flow generated by the impeller 215 when rotating in a second direction of rotation. Thus, by simply changing direction of rotation of the impeller 215 by changing direction of the motor 225 rotation, air flow may be directed predominantly from either the first axial outlet 285 or the second axial outlet 286 of the housing. In a preferred embodiment, the impeller 215 is a symmetric impeller and the first and second stator rings 281, 282 are identical but for one stator ring being inverted by 180 degrees on the rotational axis of the impeller relative to the other stator ring, such that rotation of the impeller in a first direction of rotation generates a first flow of gases from the first outlet and a second flow of gases from the second outlet, and rotation of the impeller in the opposite second direction of rotation generates the first flow of gases from the second outlet and the second flow of gases from the first outlet. The first flow of gases is greater than the second flow of gases. In other words, in the first direction of rotation a particular flow rate is provided via the first outlet 285, and in the second direction of rotation the same flow rate is provided by the second outlet 286, for a given impeller speed. However, in alternative embodiments the impeller and/or stator rings may be arranged to provide different flows from the first and second axial outlets for a given speed in the first and second rotational directions.

Figure 16:
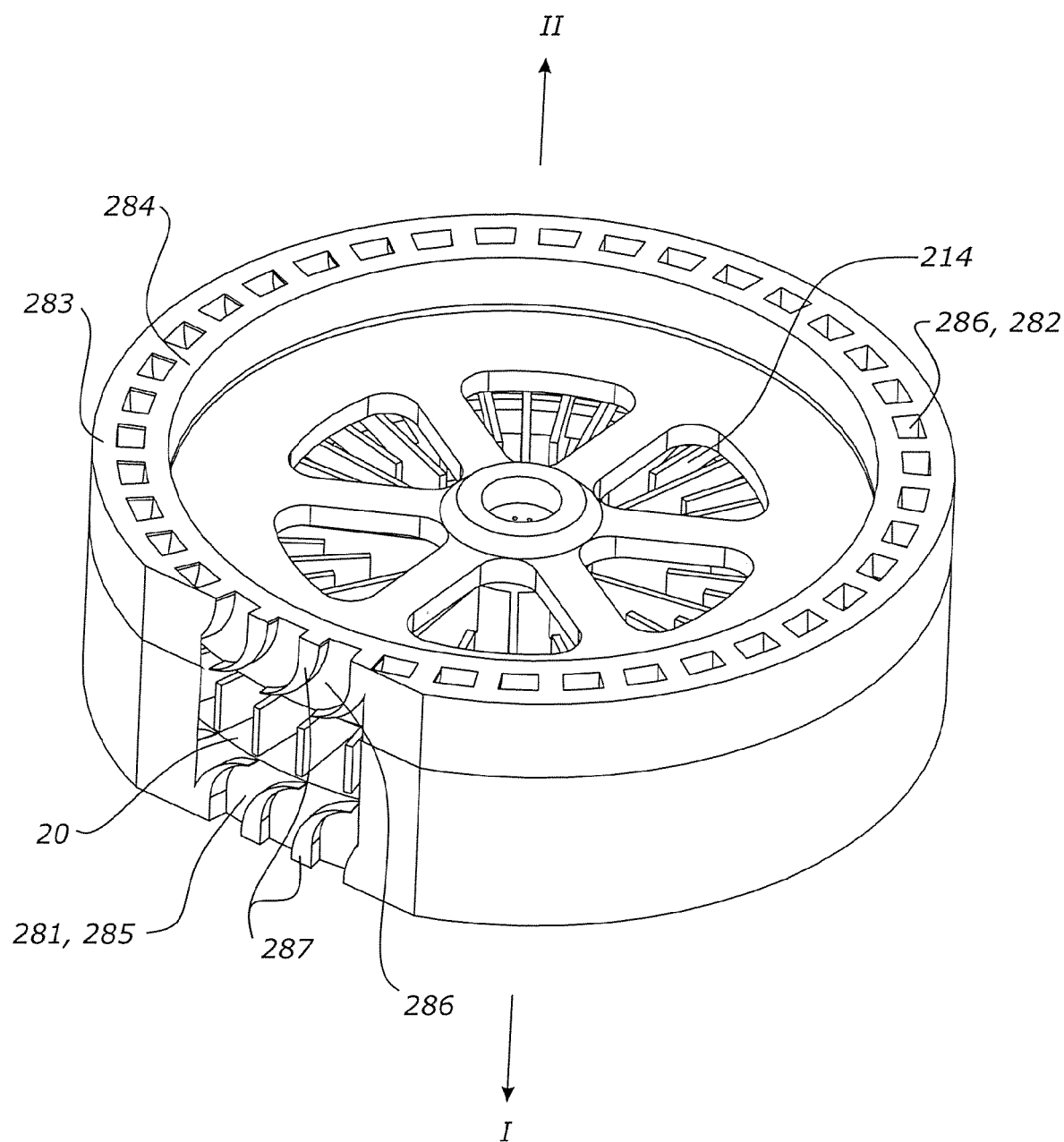
FIG. 16 shows a sectional view of the blower of FIG. 13 with a section cut on line XVI-XVI shown in FIG. 13 which is on a plane adjacent an outer dimeter of an impeller of the blower to show volute paths providing first and second axial outlets of the blower.

As best shown in FIG. 16, the volute paths 285 in the first stator ring curve 281 from the impeller chamber 20 from a tangential direction of the impeller 215 rotating in the first direction of rotation and towards a first axial direction I of the blower. The volute paths 286 in the second stator ring 282 curve from the impeller chamber 20 from an opposite tangential direction of the impeller rotating in the second opposite direction of rotation and towards a second axial direction II of the blower. In other words, the volute paths 285 of the first stator ring curve from the first axial direction I towards a tangential direction of the impeller rotating in the second rotational direction, and the volute paths 286 of the second stator ring 282 curve from the second axial direction II towards an opposite tangential direction of the impeller rotating in the first rotational direction.

Also as best shown in FIG. 16, in each stator ring 281, 282, each volute path 285, 286 is separated from an adjacent volute path by a curved rib or vane 287. In some embodiments, each curved rib 287 has a width extending in the circumferential direction of the stator ring that increases along the axial length of the rib from the impeller chamber towards the axial outlet end of the rib. In some embodiments, the circumferential width of the curved rib 287 tapers to a point at the impeller chamber end of the rib.

The motor 225 is controlled using a power supply and a controller to rotate the impeller to create the desired output air flow (both pressure and/or flow rate). Air is drawn through the apertures 213, 214 forming the axial inlets by rotation of the impeller, including over the motor to provide cooling, and directed to the first and second stator rings 281, 282 via the impeller blades. In a first direction of rotation more of a tangential velocity component of the air flow generated by the impeller is received by the first stator ring 281 than the second stator ring 282 so that a larger pressure/flow is generated at the first axial outlet 285 than at the second axial outlet 286. In a second direction of rotation more of a tangential velocity component of the air flow generated by the impeller is received by the second stator ring 282 than the first stator ring 281 so that a larger pressure/flow is generated at the second axial outlet 286 than at the first axial outlet 285. Thus, in some embodiments, rotation of the impeller in a first direction of rotation generates a first flow of gases from the first outlet 285 and a second flow of gases from the second outlet 286, wherein the first flow of gases is greater than the second flow of gases. Each stator ring slows the flow to create pressure, and the flow is directed axially out the stator ring/axial outlet of the blower.

In some embodiments the blower may comprise a single axial inlet only. For example, the blower may comprise the first axial inlet 213 only, comprising the gaps or apertures 213 between the ribs 278 supporting the first hub 276 from the first annular wall 273. The second wall 274 may be a disk or plate or continuous cover extending within the circumferential wall 275 of the housing 270, with the second central hub 277 formed at a centre of the second wall 274 and without ribs and corresponding apertures around the second central hub. Alternatively, the blower may comprise the second axial inlet 214 only, comprising the gaps or apertures 214 between the ribs 279 supporting the second hub 277 from the second annular wall 274. The first wall 273 may comprise an annular wall section and a recessed wall section radially within the annular section for receiving the motor 225, with the first central hub 276 formed at a centre of the recessed section and without ribs and corresponding apertures around the first central hub.

Figure 19:
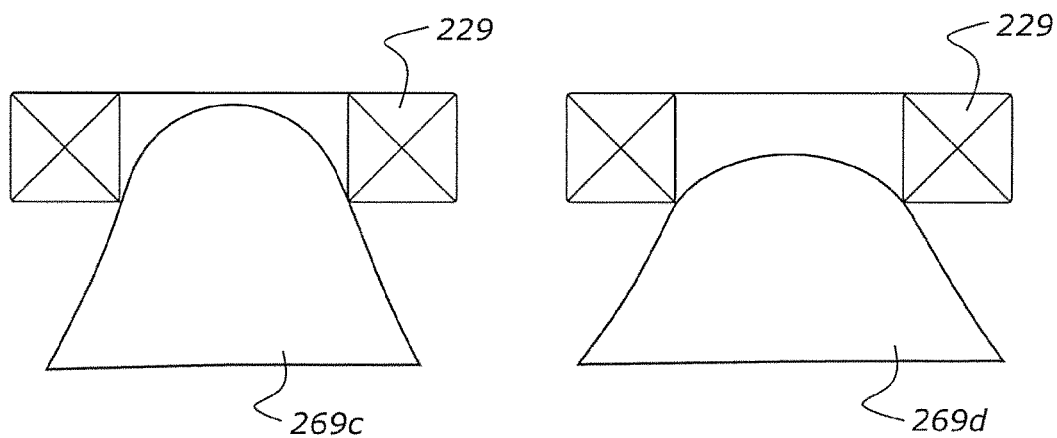
FIG. 19 shows alternative bearing support configurations for a blower shaft and impeller.

Referring to FIG. 19, in another alternative, the stub axles might not extend through the bearings. Rather each stub axle might only partially extend into (e.g. see stub axle 269c), or just contact (e.g. see stub axle 269d) the bearing. These arrangements still provide sufficient support and allow for rotation.

Other topologies of motors are possible, and those described are exemplary only. For example, a brushed or brushless DC motor, AC motor, inductance motor or variable reluctance motor could be used. The rotor and stator could take other forms to that described.

The dual axial embodiment described has a number of advantages. It provides a reduced footprint blower, both in profile and/or plan. A smaller foot print allows for a smaller housing. One reason for the smaller foot print is that the stator rings allow for a volute chamber or chambers to be omitted, reducing overall diameter and/or height of the blower, and also increases the ratio of blade length to housing diameter (that is, the space for blade length is not reduced due to the presence of a volute chamber allowing the blade length to use more of the available footprint diameter than a housing with a volute chamber).

The embodiment also allows for the use of a smaller impeller (that is, smaller in diameter, thickness and/or weight). This in turn leads to a smaller/lighter blower and/or a blower with a lower inertia. A smaller/lighter topology enables the blower to be used in portable, miniaturised and/or head or mask mounted CPAP, high flow therapy or other breathing apparatus.

As an example, the impeller might have a diameter of about 47 mm inside an about 48 mm diameter ring providing a ratio of blade length to housing diameter of 98%. Another example is about 18 mm blades in an about 20 mm radius housing for a 90% ration. These are just illustrative examples and other diameters are possible. A typical envelope/footprint of the blower could be:

Diameter: <=about 52 mm
Height: <=about 20 mm
Weight: <=about 50 g (for example 27 g)

Small impellers of these dimensions have not been suitable for use in the applications described above. This is because, when operated at the usual speeds (revolutions per minute), the air flow characteristics are insufficient to provide required therapy (for example, the flow rate and/or pressure generated by smaller impellers of this nature are not sufficient). Further, it has not been possible to run these impellers at high speeds to create the required flow rates and/or pressures, because those speeds create a number of disadvantages. For example, with increased speed, the bearings operate at a higher speed and/or temperature. This requires the use of special bearings, such as ceramic, air or fluid bearings, which are more expensive. Smaller diameter bearing races and bearings need to be used to reduce the speed of the bearings. This leads to a necessary drop in the shaft diameter, so that the shaft can still go through the centre of the bearing race. When using a smaller diameter shaft, it is much more difficult to attach the impeller and/or rotor magnet, for example through integral design or a friction fit. The manufacturing tolerances are too precise for this to be done in a viable manner. Therefore, accommodating a smaller impeller up to now has been impracticable. Another alternative is to use a blower with multiple impeller stages, however that is more expensive, larger and is more difficult to manufacture.

Figure 13:
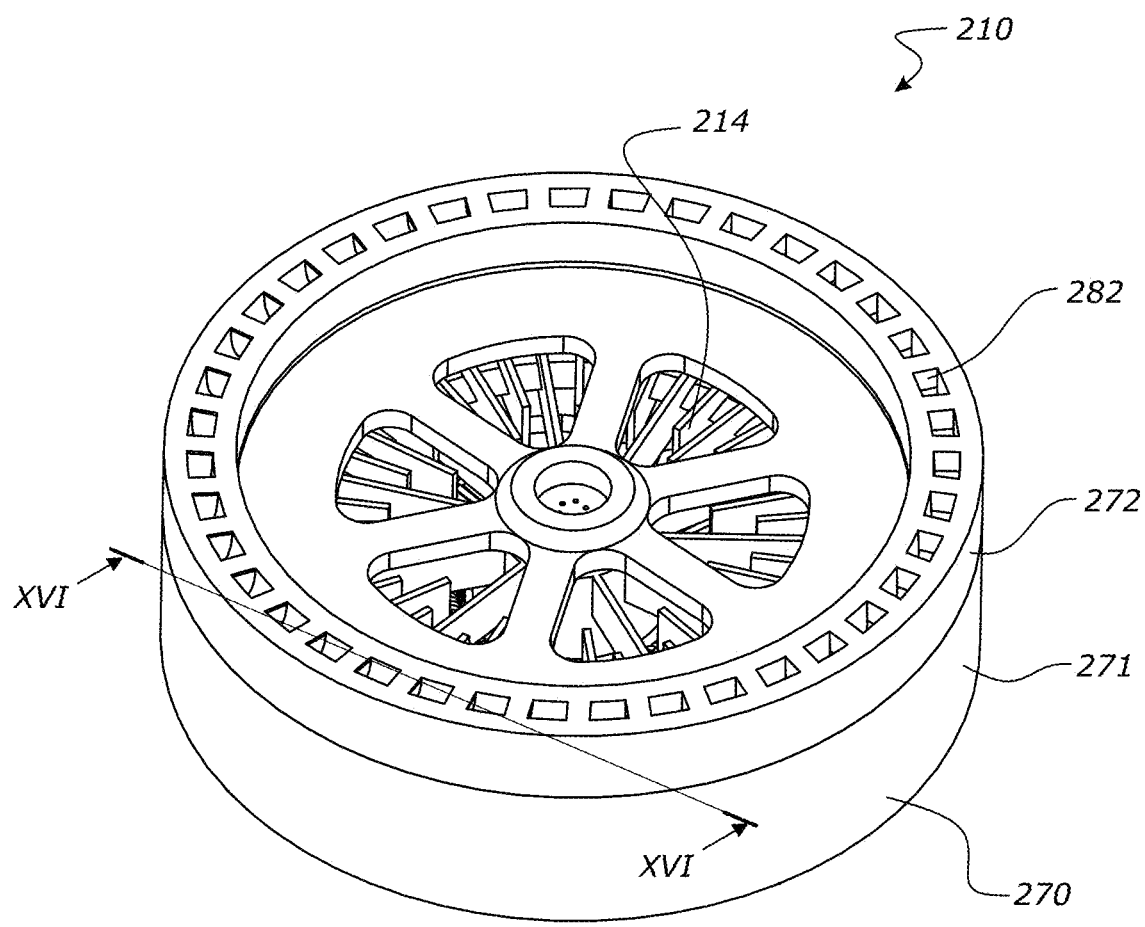
FIG. 13 shows an axial outlet blower in accordance with at least one of the embodiments disclosed herein.
Figure 14:
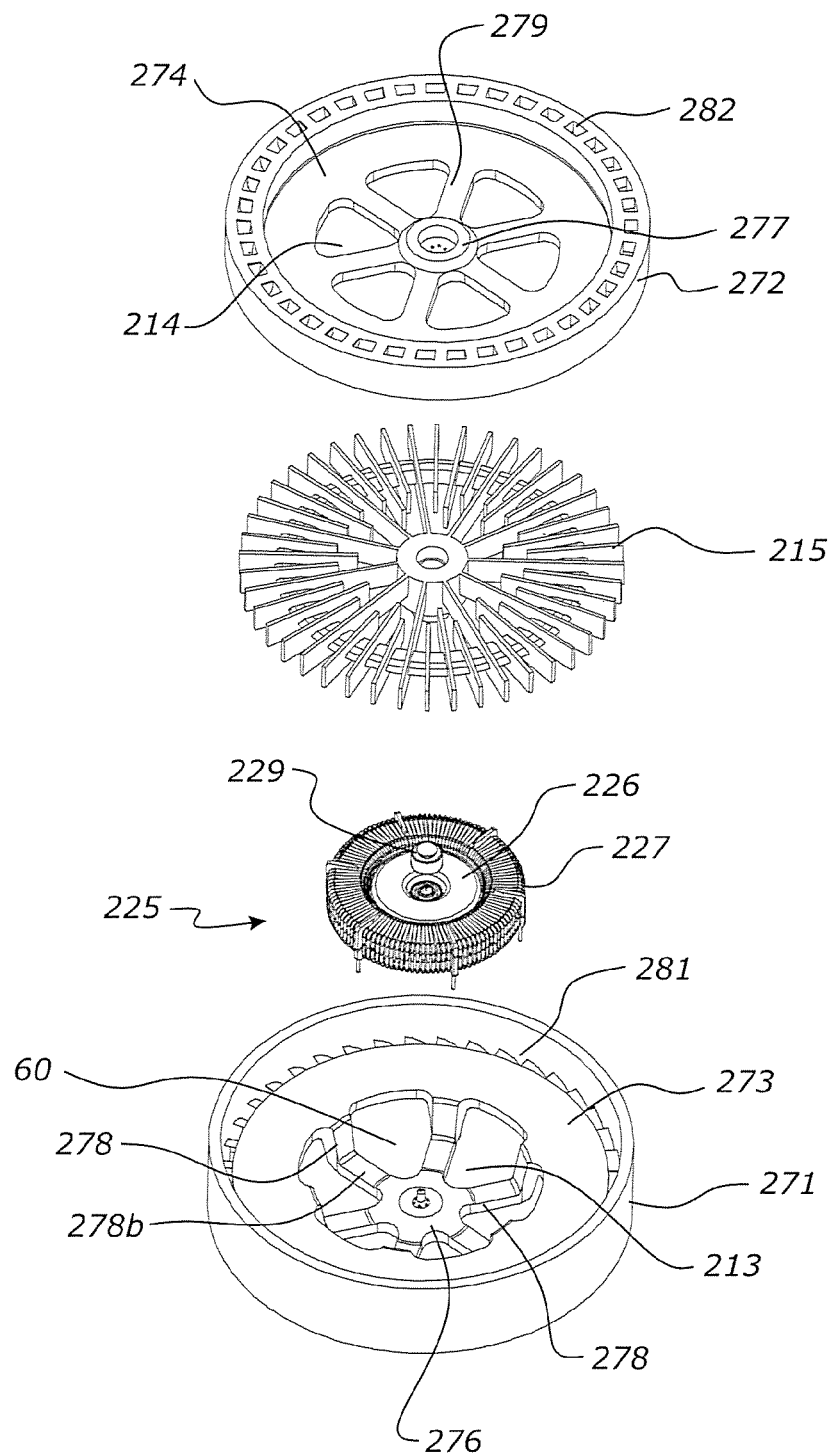
FIGS. 14 and 15 show exploded views of the blower of FIG. 13, shown from a side and from each end of the blower.
Figure 15:
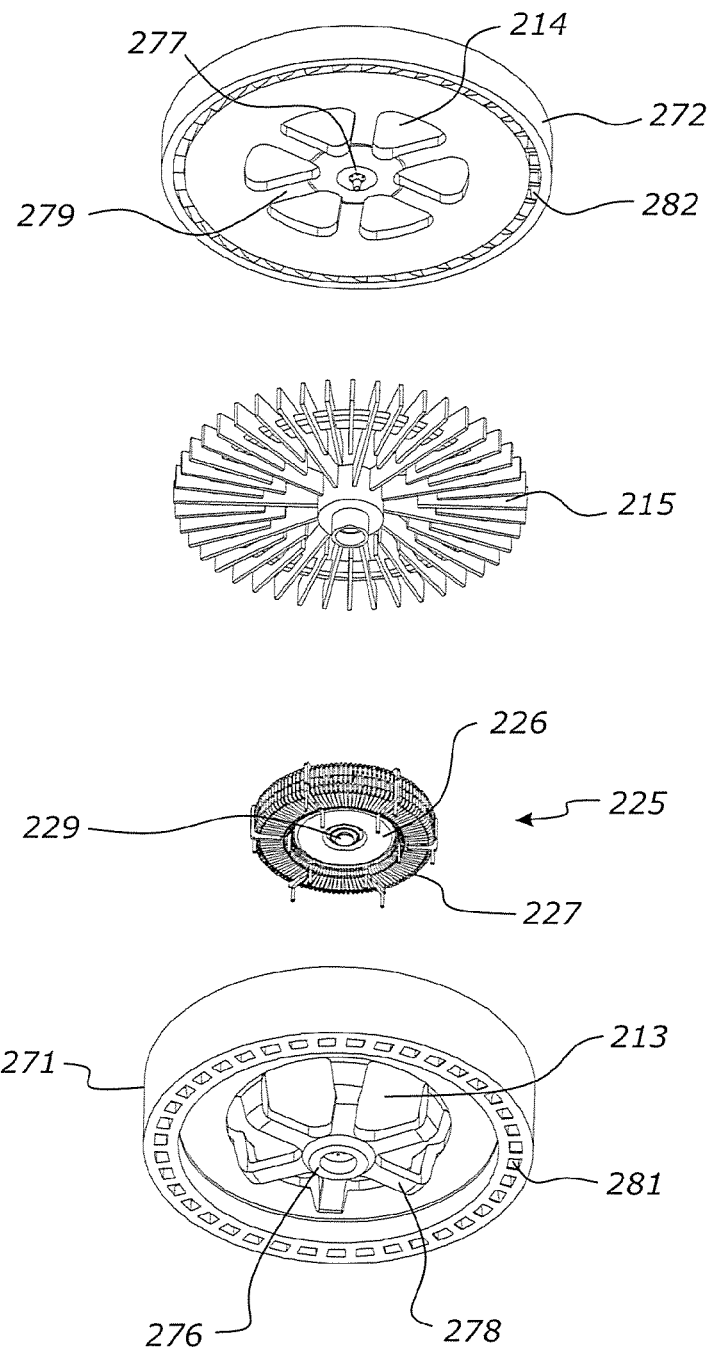

The embodiment of FIG. 13 may overcome one or more of these issues and allow for the use of a smaller impeller in a single-stage blower. The shaft that is used is hollow, or at least partially hollow. Bearings are fitted to the inside of the shaft. This allows for two things. First it allows for the shaft diameter to be of the same or similar size as previously, so that an impeller and/or rotor (or magnet) can be integrated into or fitted to a shaft in the usual manner; and second because the bearings are disposed internally, it allows for smaller diameter bearings (while still having the same is diameter shaft) to be used. This then allows the impeller to be spun at higher speeds to create the required flow rate and/or pressure with a smaller diameter impeller. But, despite the impeller/shaft being run at higher speeds, the smaller diameter bearings run at a lower speed than would larger diameter bearings traditionally used, which avoids the problems with higher speeds mentioned above. The stub axles therefore allow for connection to the internal races of the bearings, and the compliance/resilience of the stub axles allow for compliance when the shaft spins. The arrangement also reduces or eliminates eddy currents in the shaft and/or bearings. The eddy currents can degrade the bearings.

In addition, the stub blades and increased air inlet numbers and/or size allow for more pressure to be generated from a smaller blade length.

The axial outlet eliminates the need for a tangential outlet duct, which can increase the blower footprint.

The arrangement also allows for a single stage (dual) axial input/dual axial output blower, which provides for a reduced footprint or lower (low) profile. The embodiment described does not have a volute chamber which reduces the size also. The stator rings create static pressure. In some embodiments the axial airflow inlet allows for cooling of the motor stator.

Figure 23:
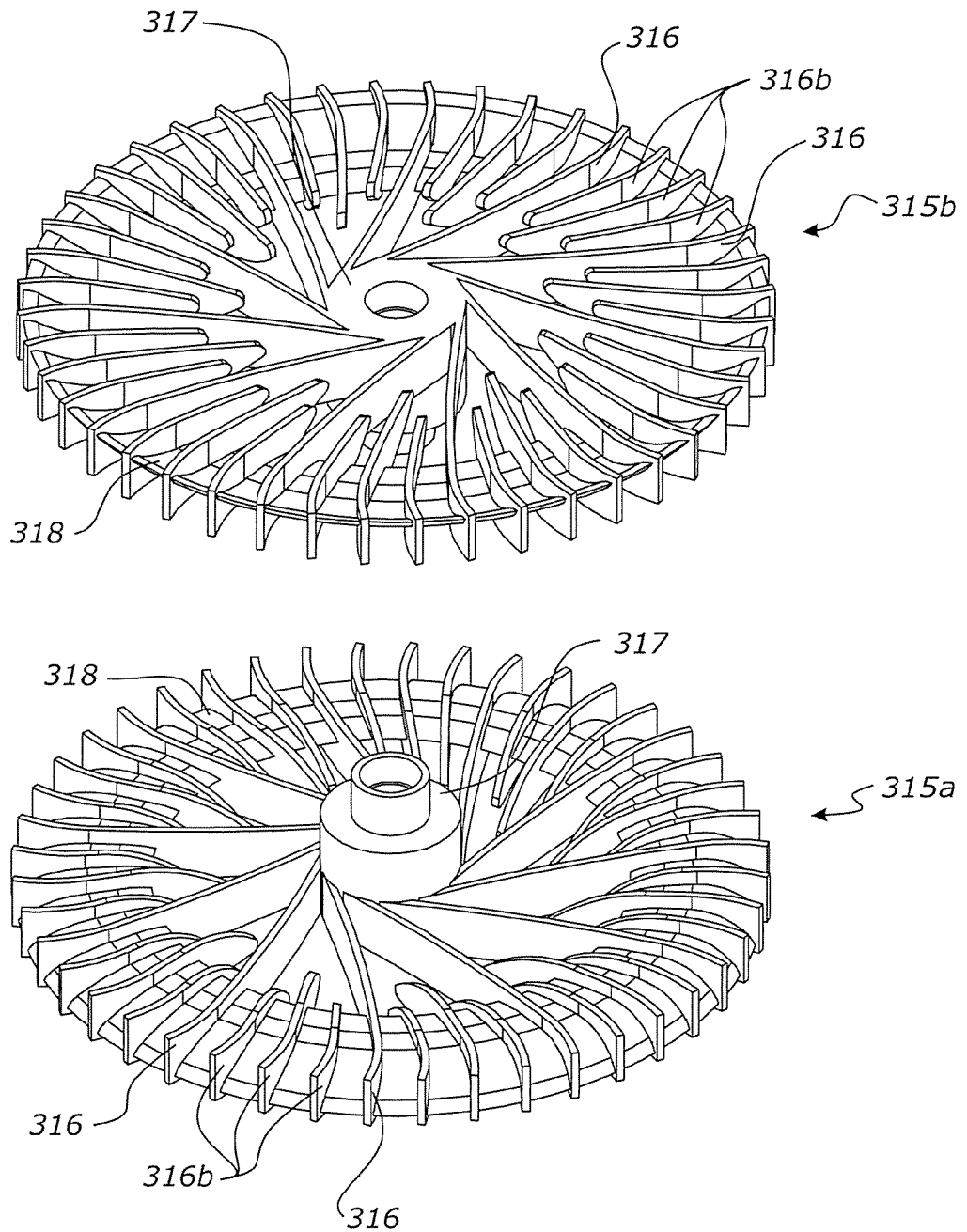
FIG. 23 shows an impeller of the blower of FIG. 20, viewed from one side and each end of the impeller.

In a further embodiment now described with reference to FIGS. 20 to 24, a dual axial outlet blower 310 may comprise two impellers 315a and 315b, as illustrated in FIG. 23. The two impellers are axially spaced apart. The housing 370 comprises a first impeller chamber 20a for receiving a first impeller 315a, and a second impeller chamber 20b for receiving a second impeller 315b.

The housing comprises a first wall 373a and a second wall 374a axially spaced apart by a circumferential wall 375a. The first and second walls and the circumferential wall combine to form the first impeller chamber 20a for receiving the first impeller 315a, as described above in relation to the earlier single impeller embodiment.

Additionally, the housing 370 comprises a third wall 373b and a fourth wall 374b axially spaced apart by a second circumferential wall 375b. The third and fourth walls and the second circumferential wall combine to form the second impeller chamber 20b for receiving the second impeller 315b. In the illustrated embodiment the first, second, third and fourth walls are annular. The first and second impeller chambers 20a, 20b may be identical but for one impeller chamber being inverted by 180 degrees on the rotational axis of the impellers relative to the other impeller chamber.

The housing further comprises a first central hub 376 and a second central hub 377. In some embodiments, the first central hub is connected via radial ribs 378 to an inner perimeter of the first annular wall 373a. In some embodiments, the second central hub 377 is connected via ribs 379 to an inner perimeter of the third annular wall 373b. Preferably the ribs connecting each hub to the respective annular wall extend radially between the hub and annular wall.

The first hub 376 provides at least a partial support for a first bearing 229, which in turn provides support for a rotor 226 and dual impeller 315a, 315b assembly. Apertures or gaps 313 between ribs 378 provide a first axial inlet. The second central hub 377 provides at least a partial support for a second bearing 229, which in turn also provides support for the rotor 226 and dual impeller 315a, 315b assembly. In some embodiments, apertures or gaps 314 between ribs provide a second axial inlet.

Figure 20:
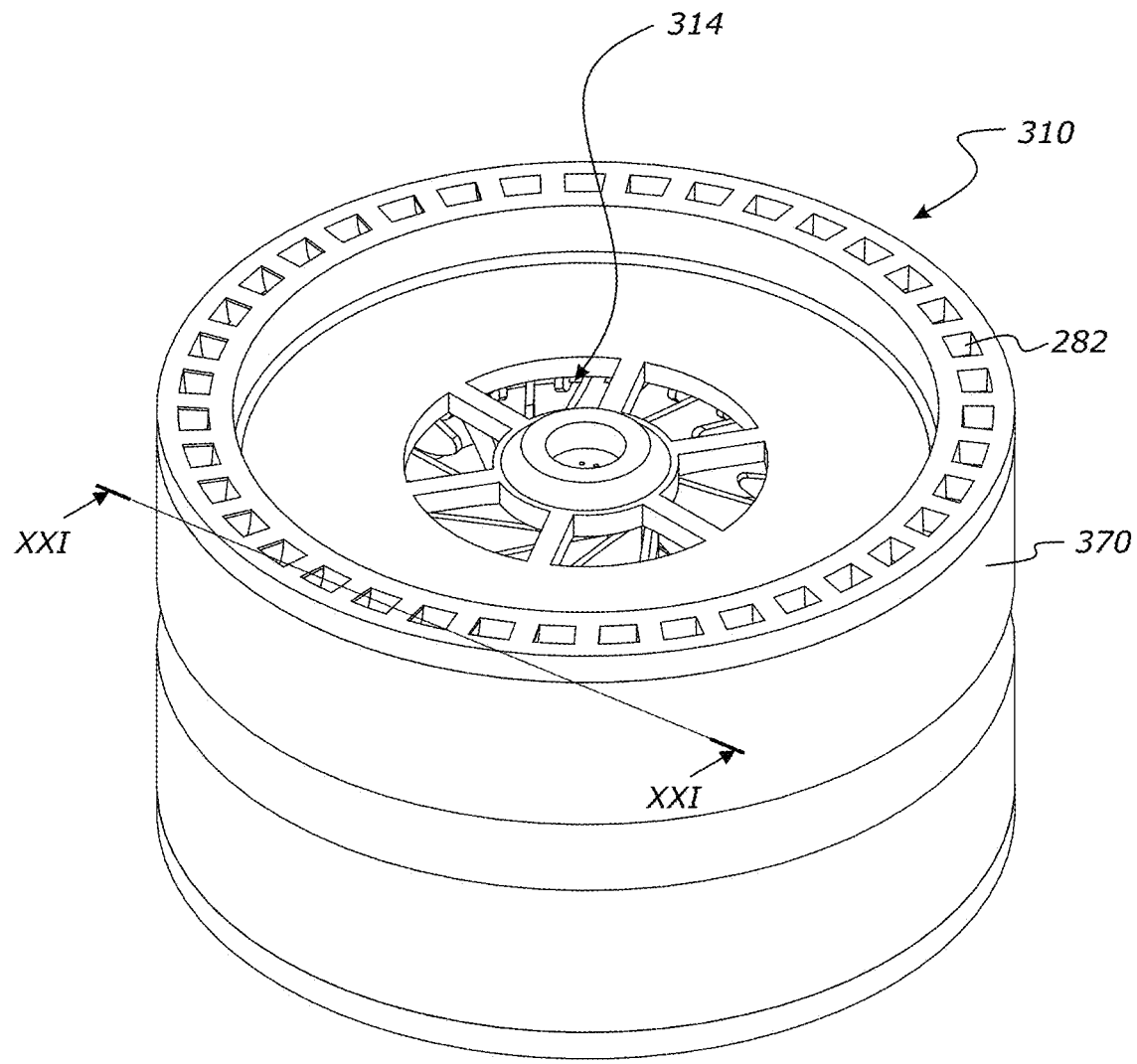
FIG. 20 shows an axial outlet blower in accordance with at least one of the embodiments disclosed herein.
Figure 21:
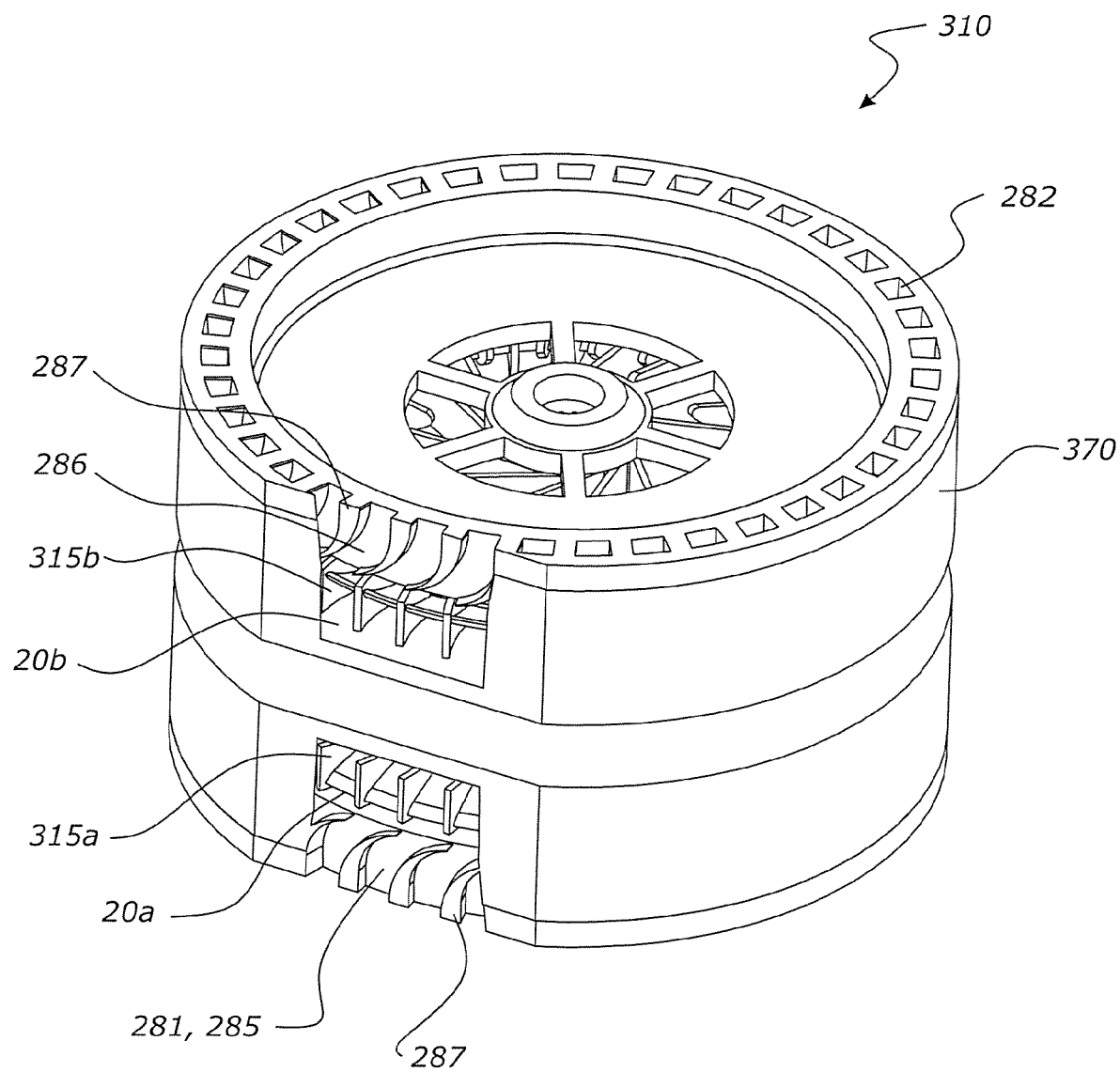
FIG. 21 shows a sectional view of the blower of FIG. 20 with a section cut on line XXI-XXI shown in FIG. 20 which is on a plane adjacent an outer dimeter of a first and a second impeller of the blower to display volute paths providing first and second axial outlets of the blower.
Figure 22:
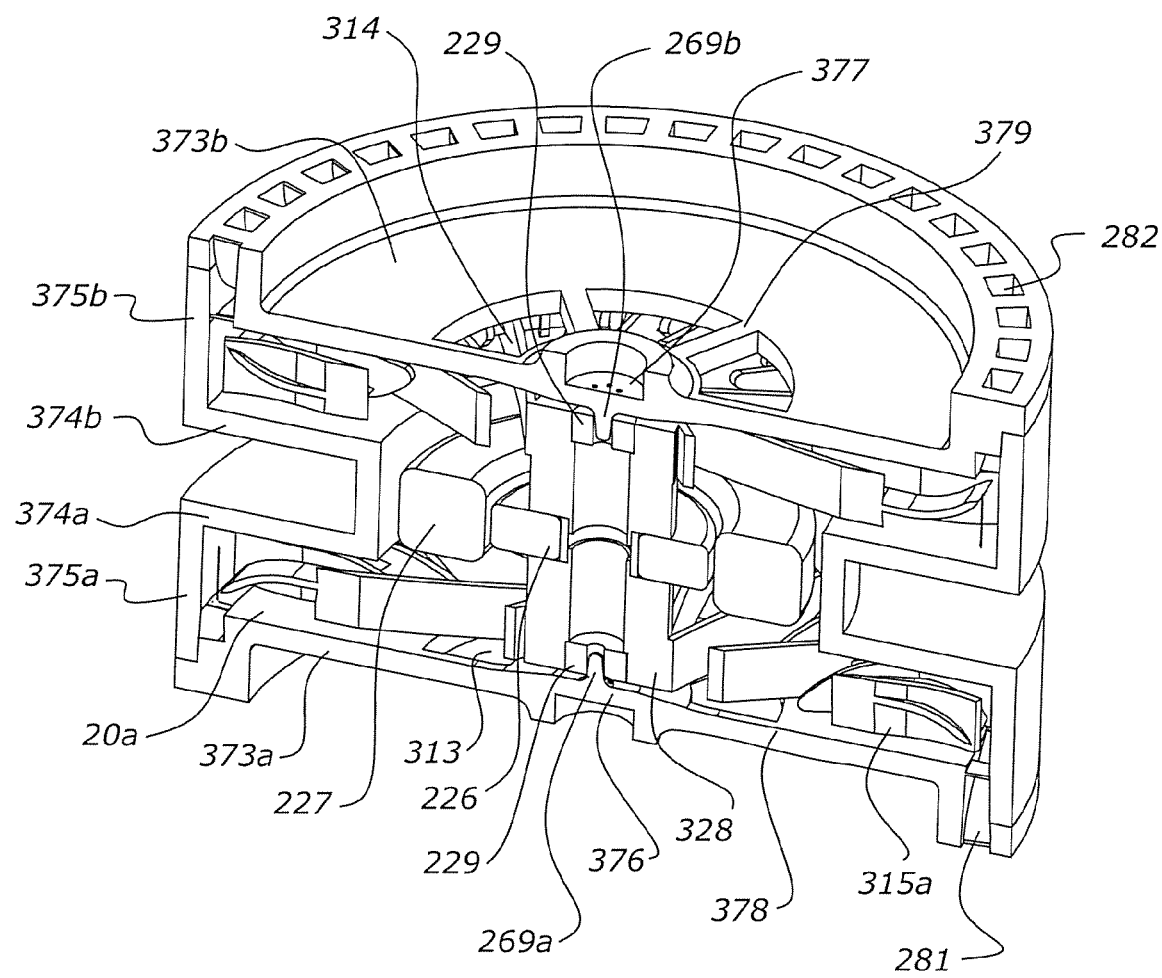
FIG. 22 shows a section view of the blower of FIG. 20 with a section plane through a centre of the blower.

In the embodiment of FIG. 20, the housing 370 comprises a single motor chamber 60. A motor comprising a stator 227 and rotor 226 is located in the motor chamber. The motor chamber and motor are located axially between the first impeller chamber 20a and the second impeller chamber 20b. By example and as illustrated, the motor chamber 60 may be provided by a circumferential wall extending between the second and fourth walls of the housing 370. The rotor 226 is coupled to the first and second impellers 315a and 315b, so that the rotor and the first and second impellers rotate together.

Figure 24:
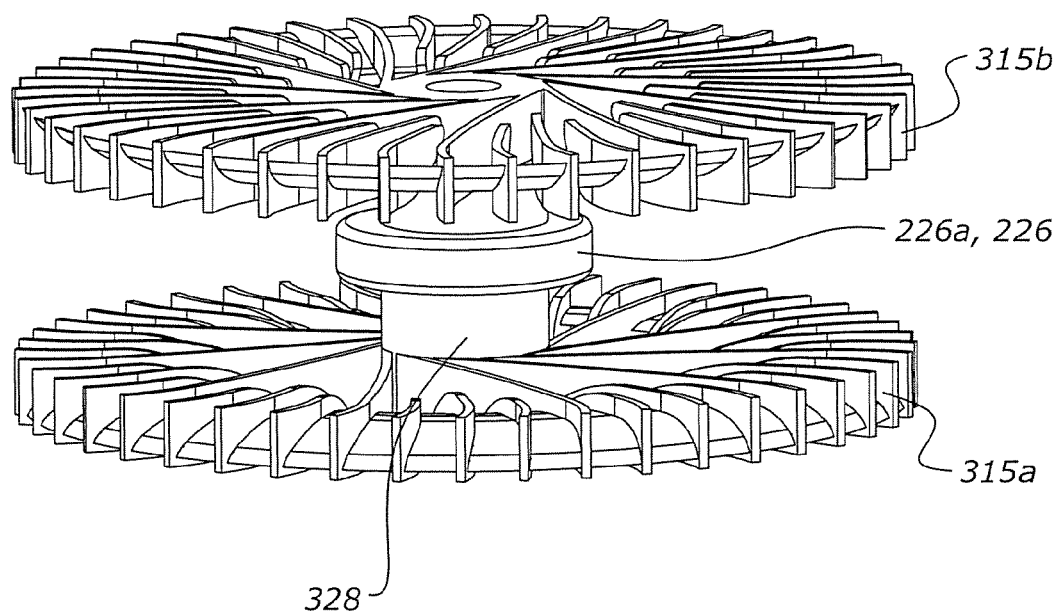
FIG. 24 shows a dual impeller and rotor assembly of the blower of FIG. 20.

An example rotor and dual impeller configuration for use in the blower 310 is shown in FIG. 24. The rotor and impeller arrangement may be similar or the same as that described above with reference to FIG. 17, but with a shaft 328 of sufficient length to support the rotor magnet 226a midway along the shaft 328 and with the first and second impellers 315a, 315b located at respective ends of the shaft or on the shaft on either axial side of the rotor magnet. The shaft may be formed in two parts press fit or otherwise secured together within or to the rotor. Each part of the shaft may be press fit or otherwise connected to or integrally formed with a respective one of the two impellers. The rotor is positioned inside stator 227 and supported by bearing elements on stub axles 269a, 269b at the first and second hubs 376, 377 as described for the earlier embodiment of FIG. 13 comprising a single impeller. A resilient mount may be provided to mount the stator within the motor chamber 60.

The first and second impellers 315a, 315b may be identical, but with one impeller being inverted by 180 degrees on the rotational axis of the impeller relative to the other impeller. An exemplary first and second impeller is shown in FIG. 23 in more detail (wherein the first and second impellers are identical). The impeller 315a, 315b comprises a hub portion 317 and flat forward swept (full-length) blades (sometimes called "vanes") 316, which radially extend from and connect to the hub portion. (Alternatively, the blades could be backward swept or radial). Each blade comprises a vertical (parallel to the rotational axis) flat portion extending from the hub 317. An annular rib/ring 318 is formed into the blades 316 and extends between them to provide rigidity at the perimeter of the blades. The ring curves towards the respective stator ring outlet 381, 382 to provide rigidity to the blades and also direct airflow through the corresponding stator ring. A plurality of short stub (partial-length) blades 316b (also termed "splitter blades") that extend part-way to the hub are interspaced between the full length blades 316. In the illustrated exemplary embodiment, there are three stub blades in-between each pair of adjacent full length blades. The annular rib 318 is also formed into and extends between the stub blades 316b, thus supporting them. The stub blades provide additional pressure normally achieved with additional blades, without the requirement for material to extend to the hub which reduces air space at the hub. Reducing airspace at hub reduces the maximum flow capability of the blower 310. If the number of blades is too high (and therefore there is too little air space at the hub due to too many blades), inlet flow is occluded, which restricts the outlet airflow of the blower. Thus the impeller of FIG. 23 has the same associated benefits as described above in relation to the single impeller dual axial outlet blower described above with reference to FIGS. 13 to 19, however is further optimised with forwardly curved blades with respect to a rotational direction to preferentially generate pressure dependent on the direction of rotation.

The housing comprises a first stator ring 281 that encircles the first annular wall 373, and a second stator ring 282 that encircles the third annular wall 373b. The stator rings 281, 282 are as described above in relation to the single impeller embodiment of FIG. 13. The first impeller 315a is arranged so that the ring 318 of the impeller curves to the volute paths 285 of the first stator ring 281, and the second impeller 315b is arranged so that the ring 318 of the impeller curves to the volute paths 286 of the second stator ring 282.

When the rotor 226 and first and second impeller 315a, 315b assembly rotates, the first impeller generates a pressure and flow at the first stator ring 281 and the second impeller generates a pressure and flow at the second stator ring 282. However with respect to a first direction of rotation, the blades of the first impeller 315a are swept or curved forwards and the blades of the second impeller 315b are swept or curved backwards. Due to the opposite curvature of the blades of the first and second impellers, when rotating in a first direction of rotation the first impeller generates a greater pressure at the first stator ring 281 than the second impeller generates at the second stator ring 282. And, when rotating in a second direction of rotation the second impeller generates a greater pressure at the second stator ring 282 than the first impeller generates at the first stator ring 281. Furthermore, the volute paths of the first stator ring are arranged to receive a larger portion of a tangential component of velocity of air flow from the first impeller when rotating in the first direction of rotation compared to when rotating in the second direction of rotation. And the volute paths of the second stator ring are arranged to receive a larger portion of a tangential component of velocity of air flow from the second impeller when rotating in the second direction of rotation compared to when rotating in the first direction of rotation. Thus when the rotor and first and second impeller assembly is rotating in the first direction of rotation, a larger pressure and/or flow is generated from the first axial outlet compared to the second axial outlet. And when the rotor and first and second impeller assembly is rotating in the second direction of rotation, a larger pressure and/or flow is generated from the second axial outlet compared to the first axial outlet. Thus, in some embodiments, rotation of the impeller in a first direction of rotation generates a first flow of gases from the first outlet 285 and a second flow of gases from the second outlet 286, wherein the first flow of gases is greater than the second flow of gases.

In some embodiments, the volute paths 285 of the first stator ring 281 extend from the first impeller chamber 20a to receive at least a substantial portion of a tangential component of velocity of air flow generated by the first impeller when rotating in a first direction of rotation, and the volute paths 286 of the second stator ring 282 extend from the second impeller chamber 20b to receive at least a substantial portion of a tangential component of velocity of air flow generated by the second impeller when rotating in a second direction of rotation. Thus, by simply changing direction of rotation of the rotor and first and second impeller assembly by changing direction of the motor rotation, air flow may be directed predominantly from either the first axial outlet or the second axial outlet of the housing. In a preferred embodiment, the first impeller 315a and the first stator ring 281 are identical to the second impeller 315b and the second stator ring 282 but for one impeller and stator ring being inverted by 180 degrees on the rotational axis of the impeller relative to the other impeller and stator ring, such that rotation of the impeller and rotor assembly in a first direction of rotation generates a first flow of gases from the first outlet and a second flow of gases from the second outlet, and rotation of the impeller in the opposite second direction of rotation generates the first flow of gases from the second outlet and the second flow of gases from the first outlet. The first flow of gases is greater than the second flow of gases. In other words, in the first direction of rotation a particular flow rate is provided via the first outlet, and in the second direction of rotation the same flow rate is provided by the second outlet, for a given impeller speed. However, in alternative embodiments the impeller and/or stator rings may be arranged to provide different flows from the first and second axial outlets for a given speed in the first and second rotational directions.

The motor is controlled using a power supply and a controller to rotate the impeller to create the desired output air flow (both pressure and/or flow rate). Air is drawn through the apertures of the axial inlets by rotation of the rotor and dual impeller assembly, and directed to the first and second stator rings via the first and second impellers. Each stator ring slows the flow to create pressure, and the flow is directed axially out the stator ring/axial outlet of the blower.

The axial outlet blowers described above may also comprise a first outlet manifold and a second outlet manifold. The first outlet manifold may comprise an inlet to receive flow from the outlets 282 of the first stator ring, and direct the flow from the first stator ring to an outlet of the first outlet manifold. Similarly, the second outlet manifold may comprise an inlet to receive flow from the outlets 282 of the second stator ring, and direct the flow from the second stator ring to an outlet of the second outlet manifold. The outlet of each of the first and second outlet manifolds may be a single outlet, and may be an axial outlet.

Where, in the foregoing description reference has been made to integers or components having known equivalents thereof, those integers are herein incorporated as if individually set forth.

The foregoing description of the invention includes preferred forms thereof. Modifications may be made thereto without departing from the scope of the invention as defined by the accompanying claims.

The invention claimed is:

1. A respiratory system comprising: a dual outlet blower comprising: a single impeller; and a housing comprising a first outlet configured to provide a first flow of gases and a second outlet configured to provide a second flow of gases, the housing further comprising an impeller chamber in which the impeller rotates; wherein the first outlet of the blower provides the first flow of gases to one of a pair of nasal outlets of a nasal interface and the second outlet provides the second flow of gases to the other one of the pair of nasal outlets of the nasal interface, or wherein the first outlet provides the first flow of gases to a nasal outlet of an oro-nasal interface or to an oral outlet of the oro-nasal interface and the second outlet provides the second flow of gases to the other one of the nasal outlet of the oro-nasal interface or the oral outlet of the oro-nasal interface; wherein the first outlet is arranged to direct the first flow of gases from the housing when the impeller rotates in a first direction of rotation, and the second outlet arranged to direct the second flow of gases from the housing when the impeller rotates in an opposite second direction of rotation.

2. A respiratory system as claimed in claim 1, wherein: with the rotation of the impeller in the first direction of rotation, the first flow of gases from the first outlet is greater than the second flow of gases from the second outlet, and with the rotation of the impeller in the second direction of rotation, the second flow of gases from the second outlet is greater than the first flow of gases from the first outlet.

3. A respiratory system as claimed in claim 1, wherein:
   the rotation of the impeller in the first direction of rotation generates the first flow of gases from the first outlet and a third flow of gases from the second outlet, and
   the rotation of the impeller in the opposite second direction of rotation generates the second flow of gases from the second outlet and a fourth flow of gases from the first outlet, and
   a flow rate of the first flow of gases is greater than a flow rate of the third flow of gases, and a flow rate of the second flow of gases is greater than a flow rate of the fourth flow of gases.

4. A respiratory system as claimed in claim 3, wherein the flow rate of the first flow of gases is substantially the same as the flow rate of the second flow of gases.

5. A respiratory system as claimed in claim 1, wherein the blower comprises a motor for driving the rotation of the impeller, and the housing comprises a motor chamber for supporting the motor within the housing.

6. A respiratory system as claimed in claim 1, wherein the impeller is a centrifugal impeller.

7. A respiratory system as claimed in claim 1, wherein the first outlet extends substantially tangentially from the housing with respect to the first direction of rotation of the impeller, and the second outlet extends substantially tangentially from the housing with respect to the opposite second direction of rotation of the impeller.

8. A respiratory system as claimed in claim 1, wherein the first outlet is a first axial outlet and the second outlet is a second axial outlet.

9. A respiratory system as claimed in claim 8, wherein the housing comprises a first stator ring and a second stator ring, each of the first stator ring and the second stator ring comprising a plurality of volute paths, the first axial outlet comprising the plurality of volute paths of the first stator ring, and the second axial outlet comprising the plurality of volute paths of the second stator ring.

10. A respiratory system as claimed in claim 9, wherein each of the first stator ring and the second stator ring comprises a plurality of curved vanes, each one of the plurality of volute paths is separated from an adjacent volute path by one of the plurality of curved vanes.

11. A respiratory system as claimed in claim 1, wherein the first outlet is a first axial outlet at a first side of the blower and the second outlet is a second axial outlet at a second side of the blower.

12. A respiratory system as claimed in claim 1, further comprising: the nasal interface, the pair of nasal outlets comprising: a first nasal outlet for providing the first flow of gases to a user via one of the user's nares, and a second nasal outlet for providing the second flow of gases to the user via the other one of the user's nares, wherein the first outlet of the blower is in fluid communication with the first nasal outlet of the nasal interface, and the second outlet of the blower is in fluid communication with the second nasal outlet of the nasal interface, wherein rotation of the impeller of the blower in the first direction of rotation generates the first flow of gases to the first nasal outlet of the nasal interface, and rotation of the impeller in the second direction of rotation generates the second flow of gases to the second nasal outlet of the nasal interface, the second direction opposite to the first direction.

13. A respiratory system as claimed in claim 12, further comprising one or more sensors to determine occlusion of one of the nares of the user and a controller to control the direction of rotation of the impeller in response to the determination of occlusion of one of the nares of the user.

14. A respiratory system as claimed in claim 13, wherein the one or more sensors comprises a pressure or flow sensor to detect a pressure or a flow rate to or at the user's nares to determine, if the one or the other one of the user's nares is at least partially occluded.

15. A respiratory system as claimed in claim 1, further comprising: the oro-nasal interface comprising: the nasal outlet for providing the first flow of gases to a user via at least one of the user's nares, and the oral outlet for providing the second flow of gases to the user via the user's mouth, and wherein the first outlet of the housing is in fluid communication with the nasal outlet of the oro-nasal interface, and the second outlet of the housing is in fluid communication with the oral outlet of the oro-nasal interface, wherein rotation of the impeller of the blower in the first direction of rotation generates the first flow of gases to the nasal outlet, and rotation of the impeller in the second direction of rotation generates the second flow of gases to the oral outlet.

16. The respiratory system as claimed in claim 1, wherein the housing comprises a volute chamber configured to receive gases from the impeller chamber.

* * * * *

UNITED STATES PATENT AND TRADEMARK OFFICE
CERTIFICATE OF CORRECTION

| | | |
|---|---|---|
| PATENT NO. | : 11,173,263 B2 | Page 1 of 1 |
| APPLICATION NO. | : 16/097575 | |
| DATED | : November 16, 2021 | |
| INVENTOR(S) | : Bothma et al. | |

It is certified that error appears in the above-identified patent and that said Letters Patent is hereby corrected as shown below:

On the Title Page

On Page 2, Column 2 item (56) (U.S. Patent Documents), Line 39, delete "Ma" and insert --Bothma--.

In the Claims

At Column 25, Line 34, In Claim 12, delete "comprising:" and insert --comprising--.

At Column 26, Line 19, In Claim 14, delete "determine," and insert --determine--.

At Column 26, Line 21, In Claim 15, delete "interface comprising:" and insert --interface comprising--.

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*